United States Patent
Min et al.

(10) Patent No.: US 12,059,297 B2
(45) Date of Patent: Aug. 13, 2024

(54) ULTRASONIC PROBE

(71) Applicant: SAMSUNG MEDISON CO., LTD., Gangwon-do (KR)

(72) Inventors: Haekee Min, Gangwon-do (KR); Yoonsung Kyung, Gangwon-do (KR); Jongsun Ko, Gangwon-do (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 670 days.

(21) Appl. No.: 17/232,438

(22) Filed: Apr. 16, 2021

(65) Prior Publication Data

US 2021/0330290 A1 Oct. 28, 2021

(30) Foreign Application Priority Data

Apr. 22, 2020 (KR) .......................... 10-2020-0048630

(51) Int. Cl.
| | |
|---|---|
| *B06B 1/06* | (2006.01) |
| *A61B 8/00* | (2006.01) |
| *H10N 30/87* | (2023.01) |

(52) U.S. Cl.
CPC .......... *A61B 8/4444* (2013.01); *B06B 1/0622* (2013.01); *B06B 1/067* (2013.01); *H10N 30/875* (2023.02); *A61B 8/4494* (2013.01)

(58) Field of Classification Search
CPC .......................... B06B 1/0622; H10N 30/875
See application file for complete search history.

(56) References Cited

U.S. PATENT DOCUMENTS

| | | |
|---|---|---|
| 5,640,308 A | 6/1997 | Osann, Jr. et al. |
| 5,744,898 A | 4/1998 | Smith et al. |
| (Continued) | | |

FOREIGN PATENT DOCUMENTS

| | | |
|---|---|---|
| EP | 3363549 A1 | 8/2018 |
| JP | H05-142205 A | 6/1993 |
| KR | 10-0630582 B1 | 9/2006 |

OTHER PUBLICATIONS

Extended European Search Report dated Sep. 23, 2021 issued in European Patent Application No. 21168696.9.

*Primary Examiner* — Bryan P Gordon
(74) *Attorney, Agent, or Firm* — Morgan, Lewis & Bockius LLP

(57) ABSTRACT

Disclosed in an ultrasonic probe for obtaining an ultrasonic image. The ultrasonic probe includes piezoelectric elements forming a plurality of rows arranged to form a pair along a lateral direction, a kerf formed between the piezoelectric elements along the lateral direction, a first circuit layer disposed below the piezoelectric elements, a second circuit layer disposed to be spaced apart from a lower side of the first circuit layer and including a plurality of wires extending along the rows, the second circuit layer being provided with a first region in selectively contact with the piezoelectric elements and a second region disposed at opposite ends of the first region and folded without being in contact with the piezoelectric elements, and a first connection part to electrically connect the first circuit layer and the second circuit layer, wherein the first region is, when the plurality of wires extending along one row of the pair of rows extends from the first region to the second region, provided such that the plurality of wires is distributed to the other adjacent row.

19 Claims, 13 Drawing Sheets

(56) References Cited

U.S. PATENT DOCUMENTS

| | | | |
|---|---|---|---|
| 5,865,163 A | 2/1999 | Wildes et al. | |
| 7,640,651 B2 | 1/2010 | Cohen et al. | |
| 7,745,977 B2 * | 6/2010 | Aoki | A61B 8/4281 |
| | | | 310/365 |
| 10,267,766 B2 | 4/2019 | Kudyakov | |
| 2004/0100163 A1 * | 5/2004 | Baumgartner | B06B 1/0622 |
| | | | 310/334 |
| 2010/0198077 A1 * | 8/2010 | Ooura | A61B 8/08 |
| | | | 600/459 |
| 2013/0241355 A1 * | 9/2013 | Okada | B06B 1/0622 |
| | | | 29/25.35 |
| 2015/0094590 A1 * | 4/2015 | Kiyose | H10N 39/00 |
| | | | 600/447 |
| 2019/0328360 A1 * | 10/2019 | Ferin | B06B 1/0622 |

* cited by examiner

ULTRASONIC PROBE

CROSS-REFERENCE TO RELATED APPLICATION(S)

This application is based on and claims priority under 35 U.S.C. § 119 to Korean Patent Application No. 10-2020-0048630, filed on Apr. 22, 2020, in the Korean Intellectual Property Office, the disclosure of which is incorporated by reference herein in its entirety.

BACKGROUND

1. Field

The disclosure relates to an ultrasonic probe for obtaining an ultrasonic image.

2. Description of the Related Art

An ultrasonic imaging apparatus is an apparatus that irradiates an ultrasonic signal from a body surface of a target toward a target site in the body and obtains an image of a monolayer or blood flow of soft tissue without invasion by using information of a reflected ultrasonic signal (ultrasonic echo signal).

The ultrasonic imaging apparatus is small, inexpensive, real-time displayable, easy to use, and has a high level of safety because there is no radiation exposure, compared to other imaging apparatuses such as an X-ray diagnostic apparatus, an X-ray CT scanner (Computerized Tomography Scanner), an MRI (Magnetic Resonance Image) and a nuclear medicine diagnostic apparatus.

Therefore, the ultrasonic imaging apparatus has been widely used for diagnosis of the heart, abdomen, urinary system and obstetrics.

In general, an ultrasonic imaging apparatus may include a main body, and an ultrasonic probe to transmit an ultrasonic signal to an object to be diagnosed and receive a signal reflected from the object.

The ultrasonic probe may have a structure in which an ultrasonic signal transmitted from a piezoelectric layer inside the ultrasonic probe passes through a lens provided to be in contact with an object and is transmitted to the object, and the ultrasonic signal reflected from the object and returned is received through the lens again.

In recent years, multi-row probes of 1.25D (3 rows) or more have been replacing 1D (1 row) probes. The multi-row probe may physically or electrically adjust a focus area, thereby realizing a high-resolution image in a wider area.

In order to implement a multi-row probe, a laminate circuit structure may be provided below a piezoelectric layer. The laminate circuit structure may be provided as a flexible printed circuit board (FPCB). When the laminate circuit structure is folded at opposite ends of the piezoelectric layer in the direction of a probe axis, a situation in which a circuit pattern on the laminate circuit structure is disconnected (open) may occur.

SUMMARY

It is an aspect of the disclosure to provide an ultrasonic probe including a plurality of piezoelectric elements forming a plurality of rows along an elevation direction.

It is another aspect of the disclosure to provide an ultrasonic probe an ultrasonic probe capable of preventing disconnection (open) due to folding of a plurality of wires corresponding to a plurality of piezoelectric elements and forming a circuit pattern on a laminate circuit structure included in a flexible printed circuit board (FPCB) disposed below the piezoelectric elements.

Additional aspects of the disclosure will be set forth in part in the description which follows and, in part, will be obvious from the description, or may be learned by practice of the disclosure.

In accordance with an aspect of the disclosure, an ultrasonic probe includes piezoelectric elements forming a plurality of rows arranged to form a pair along a lateral direction, a kerf formed between the piezoelectric elements along the lateral direction, a first circuit layer disposed below the piezoelectric elements, a second circuit layer disposed to be spaced below the first circuit layer and including a plurality of wires extending along the rows, the second circuit layer being provided with a first region in selectively contact with the piezoelectric elements and a second region disposed at opposite ends of the first region and folded without being in contact with the piezoelectric elements, and a first connection part to electrically connect the first circuit layer and the second circuit layer, wherein the first region is, when the plurality of wires extending along one row of the pair of rows extends from the first region to the second region, provided such that the plurality of wires is distributed to the other adjacent row.

The second circuit layer may be provided such that the plurality of wires is parallel in a single layer.

The piezoelectric elements may form a plurality of columns along an elevation direction, and the plurality of wires may respectively correspond to the plurality of rows.

The first region of the second circuit layer may include a plurality of sub-circuit layers laminated in an axial direction, and each of the plurality of wires may be formed in each of the plurality of sub-circuit layers.

The second circuit layer may further include a convergence layer in which the plurality of wires is gathered as one layer in the second region and extends therefrom.

The ultrasonic probe may further include a second connection part to connect each of the sub-circuit layers and the convergence layer.

The plurality of wires may be distributed from the second region, and the second connection part may be formed in the folded second region.

The first region may include a first edge region formed at one end of the first region adjacent to the second region and a second edge region formed at the other end of the first region adjacent to the second region, and the plurality of wires may be distributed from at least one of the first edge region and the second edge region.

The second connection part may be formed in at least one of the first edge region and the second edge region.

The plurality of wires extending along one row of the pair of rows may be distributed in a first direction from the first edge region, the plurality of wires extending along the other row may be distributed in a second direction from the second edge region, and the first direction and the second direction may be parallel to a direction in which the second circuit layer is folded.

The first direction and the second direction may be opposite to each other.

Circuit patterns formed by the plurality of wires may be formed in a point symmetry with respect to the center of the first region.

a distance between the plurality of wire is widened while being distributed to the first edge region or the second edge region, and the distance between the plurality of wire in the second region is greater than the distance between the plurality of wire in the first region.

At least one of the first connection part and the second connection part may include a conductive hole, and the conductive hole may be filled with a conductive material, and connect an wire formed in the first circuit layer and the plurality of wires formed in the second circuit layer.

The ultrasonic probe may further include an enhanced layer disposed between the piezoelectric elements and the first circuit layer.

At least one of the first connection part and the second connection part may electrically connect the first circuit layer and the second circuit layer or the second circuit layer and the convergence layer by at least one of conductive paste, conductive plating, sputtering, or printing.

In accordance with another aspect of the disclosure, an ultrasonic probe includes piezoelectric elements forming a plurality of rows arranged to form a pair along a lateral direction and forming a plurality of columns along an elevation direction, and a second circuit layer disposed below the piezoelectric elements and including a plurality of wires respectively corresponding to and extending from the plurality of columns along the rows, the second circuit layer being provided with a first region in selectively contact with the piezoelectric elements and a second region disposed at opposite ends of the first region and folded without being in contact with the piezoelectric elements, wherein the first region is, when the plurality of wires extending along one row of the pair of rows extends from the first region to the second region, provided such that the plurality of wires is distributed to the other adjacent row.

The second circuit layer may further include a convergence layer in which the plurality of wires is gathered as one layer in the second region and extends therefrom.

The ultrasonic probe may further include a connection part to connect each of the sub-circuit layers and the convergence layer.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Configurations shown in the embodiments and the drawings described in the present specification are only the preferred embodiments of the present disclosure, and thus it is to be understood that various modified examples, which may replace the embodiments and the drawings described in the present specification, are possible when filing the present application.

Like reference numbers or signs in the various figures of the application represent parts or components that perform substantially the same functions.

The terms used herein are for the purpose of describing the embodiments and are not intended to restrict and/or to limit the disclosure. For example, the singular expressions herein may include plural expressions, unless the context clearly dictates otherwise. Also, the terms "comprises" and "has" are intended to indicate that there are features, numbers, steps, operations, elements, parts, or combinations thereof described in the specification, and do not exclude the presence or addition of one or more other features, numbers, steps, operations, elements, parts, or combinations thereof.

Throughout the specification, when a member is described as being "on" another member, this includes not only a case where one member is adjacent to the other member, but also a case where another member is placed between the two members.

It will be understood that although the terms first, second, etc. may be used herein to describe various components, these components should not be limited by these terms, and the terms are only used to distinguish one component from another. For example, without departing from the scope of the disclosure, the first component may be referred to as a second component, and similarly, the second component may also be referred to as a first component. The term "and/or" includes any combination of a plurality of related items or any one of a plurality of related items.

The terms "front end," "rear end," "upper portion," "lower portion," "upper end" and "lower end" used in the following description are defined with reference to the drawings, and the shape and position of each component are not limited by these terms.

Hereinafter, embodiments of the disclosure will be described in detail with reference to the accompanying drawings.

Figure 1:
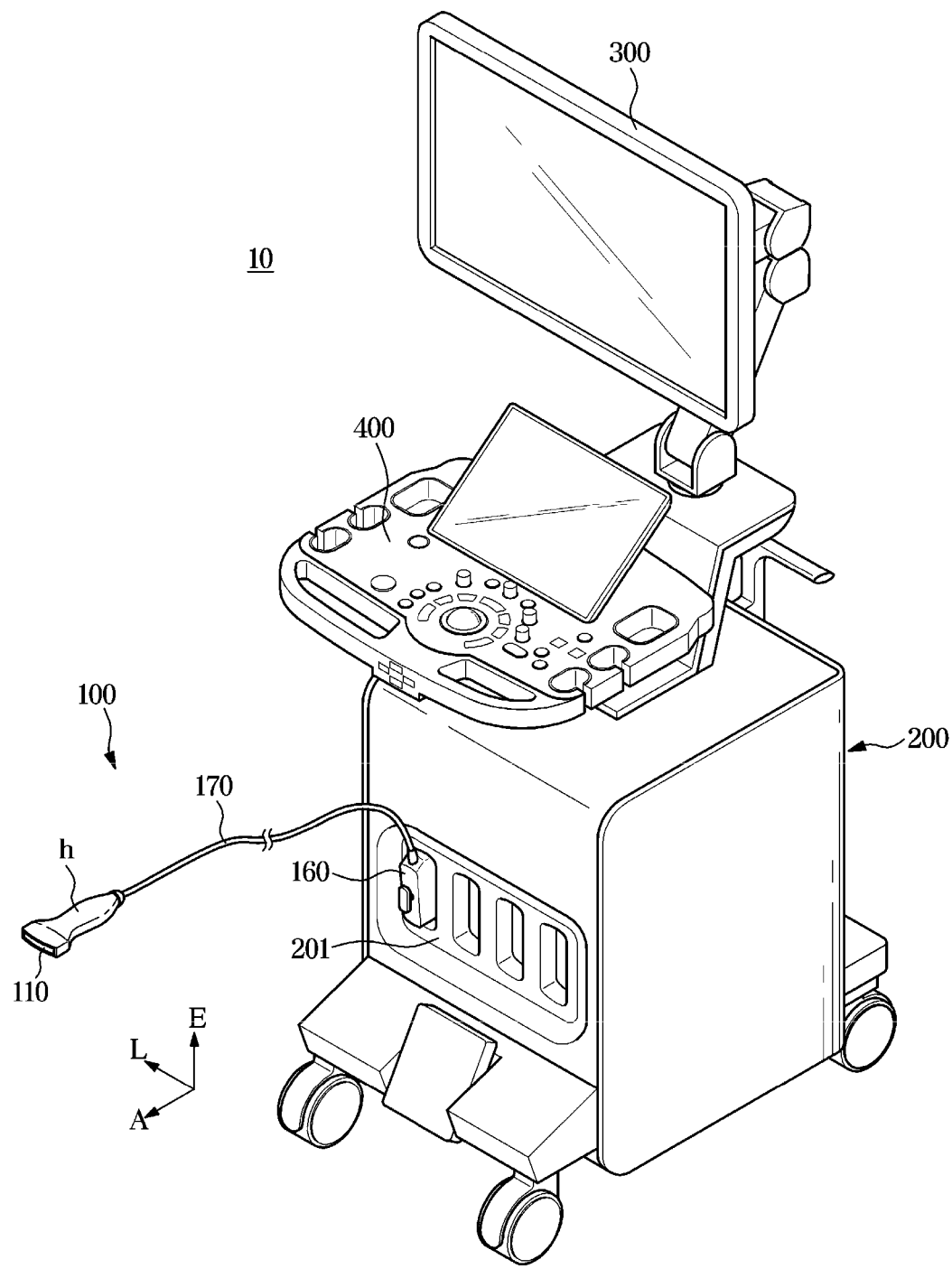
FIG. 1 is a perspective view of an ultrasonic imaging apparatus according to an embodiment.

FIG. 1 is a perspective view of an ultrasonic imaging apparatus according to an embodiment.

Referring to FIG. 1, an ultrasonic imaging apparatus 10 includes an ultrasonic probe 100 configured to transmit an ultrasonic signal to an object, receive an echo ultrasonic signal from the object and convert the echo ultrasonic signal into an electrical signal, and a main body 200 configured to generate an ultrasonic image based on the ultrasonic signal. The main body 200 may be connected to the ultrasonic probe 100 through a wired communication network or a wireless communication network. The main body 200 may be a workstation including a display 300 and an input device 400.

The ultrasonic probe 100 includes a transducer module 110 provided in a housing h to irradiate an ultrasonic wave onto an object ob, receive an echo ultrasonic wave reflected from the object ob, and convert an electrical signal and an ultrasonic wave to each other, a male connector 160 physically coupled to a female connector 201 of the main body 200 to transmit and receive signals to and from the main body 200, and a cable 170 to connect the male connector 160 and the transducer module 110.

The object ob may be a living body of a human or animal or tissues in vivo such as blood vessels, bones, muscles, and the like, but is not limited thereto, and anything may become the object ob if its internal structure may be imaged by the ultrasonic imaging apparatus 10.

The ultrasonic probe 100 may be connected to the main body 200 through a wireless communication network to receive various signals required for control of the ultrasonic probe 100 or transmit an analog signal or a digital signal corresponding to an echo ultrasonic signal received by the ultrasonic probe 100 to the main body 200. The wireless communication network refers to a communication network that may send and receive signals wirelessly.

The echo ultrasonic waves are ultrasonic waves reflected from the object ob to which the ultrasonic waves are irradiated and have various frequency bands or energy intensities for generating various ultrasonic images depending on diagnosis modes.

The transducer module 110 may generate ultrasonic waves according to an applied AC power. Specifically, the transducer module 110 may receive AC power from an external power supply device or an internal power storage device such as a battery. A vibrator of the transducer module 110 may generate ultrasonic waves by vibrating according to the received AC power.

Three directions that are perpendicular to each other with respect to the center of the transducer module 110 may be defined as an axis direction A, a lateral direction L, and an elevation direction E. Specifically, a direction in which ultrasonic waves are irradiated may be defined as the axial direction A, a direction in which the transducer module 110 forms horizontal rows may be defined as the lateral direction L, and the remaining direction perpendicular to the axial direction A and the lateral direction L may be defined as the elevation direction E. The transducer module 110 may also form a plurality of rows in the elevation direction E, and in this case, may form a multi-row array arrangement.

One end of the cable 170 is connected to the transducer module 110 and the other end of the cable 170 is connected to the male connector 160, thereby connecting the transducer module 110 and the male connector 160.

The male connector 160 may be physically coupled to the female connector 201 of the main body 200 by being connected to the other end of the cable 170.

The male connector 160 transmits an electrical signal generated by the transducer module 110 to the physically coupled female connector 201 or receives a control signal generated by the main body 200 from the female connector 201.

Hereinafter, the configuration of the ultrasonic probe will be described in more detail.

Figure 2:
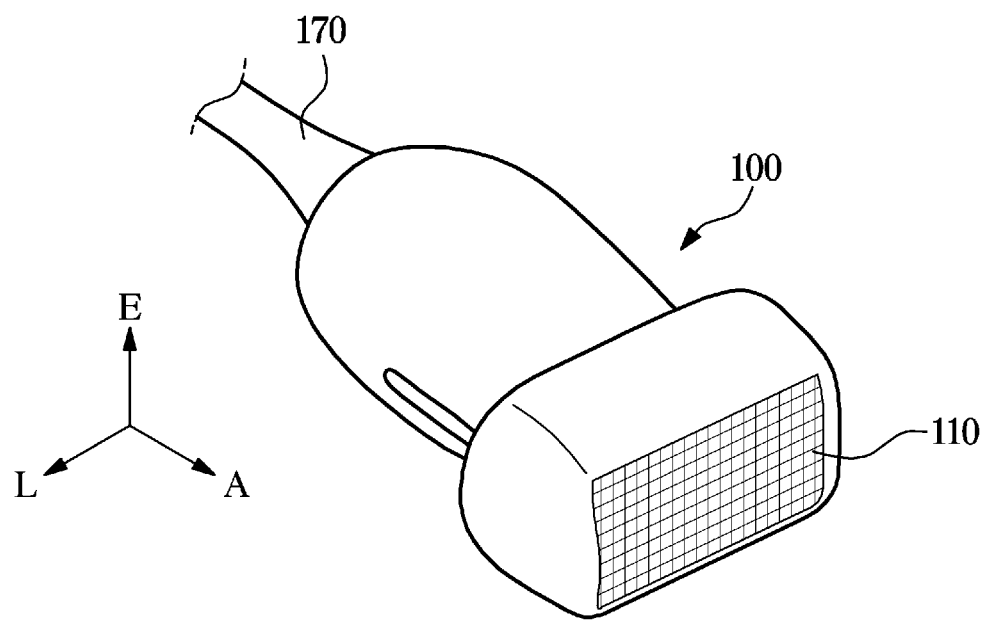
FIG. 2 is an external view of an ultrasonic probe including a multidimensional array transducer according to an embodiment.

FIG. 2 is an external view of an ultrasonic probe including a multidimensional array transducer according to an embodiment.

The ultrasonic probe 100 may transmit and receive ultrasonic signals as a part that comes in contact with the surface of an object. Specifically, the ultrasonic probe 100 may serve to transmit an ultrasonic signal to a specific portion inside the object according to a transmission signal received from the main body 200 and receive an echo ultrasonic signal reflected from the specific portion inside the object and transmit the echo ultrasonic signal to the main body 200. The echo ultrasonic signal may be an ultrasonic signal that is a radio frequency (RF) signal reflected from the object, but is not limited thereto, and includes all signals in which the ultrasonic signal transmitted to the object is reflected.

An object may be a living body of a human or animal, but is not particularly limited thereto, and anything may become an object if its internal structure may be imaged by an ultrasonic signal.

The ultrasonic probe 100 may include a transducer array to convert electrical signals and ultrasonic signals to each other in order to transmit ultrasonic signals to the inside of an object. The transducer array may be composed of a single transducer element or multiple transducer elements.

The ultrasonic probe 100 may generate an ultrasonic signal through the transducer array to transmit the ultrasonic signal to a target portion inside an object as a focus and may receive an echo ultrasonic signal reflected from the target portion inside the object through the transducer array.

When the echo ultrasonic signal reaches the transducer array, the transducer array may vibrate at a predetermined frequency corresponding to a frequency of the echo ultrasonic signal to output an AC current having a frequency corresponding to the vibration frequency of the transducer array. Accordingly, the transducer array may convert the received echo ultrasonic signal into an echo signal, which is a predetermined electrical signal.

Each of transducer elements constituting the transducer array may convert an ultrasonic signal and an electrical signal to each other. To this end, the transducer element may be implemented as a magnetostrictive ultrasonic transducer using the magnetostrictive effect of a magnetic body or a capacitive micromachined ultrasonic transducer (hereinafter abbreviated as cMUT) that transmits and receives ultrasonic waves using vibrations of hundreds or thousands of finely processed thin films.

The transducer module 110 of the ultrasonic probe 100 may be arranged linearly or in a curved surface as illustrated in FIG. 2. Although the basic operating principles of the ultrasonic probe 100 in both cases are the same, in the ultrasonic probe 100 in which the transducer module 110 is arranged in a curved surface, an ultrasonic signal irradiated from the transducer module 110 has a fan shape, so that the generated ultrasonic image may also have a fan shape.

The transducer module 110 according to an embodiment may be provided as a matrix probe. In this case, the transducer module 110 may include a multi-row type multidimensional transducer array having a plurality of rows.

For example, when the transducer module 110 includes a two-dimensional transducer array, the inside of an object may be imaged in three dimensions. However, the disclosure is not limited thereto, and the ultrasonic probe 100 may be provided in other forms known in the art other than that illustrated in FIG. 2.

Hereinafter, an internal configuration of a transducer module implemented with piezoelectric ultrasonic transducer elements according to an embodiment will be described in more detail with reference to FIG. 3.

Figure 3:
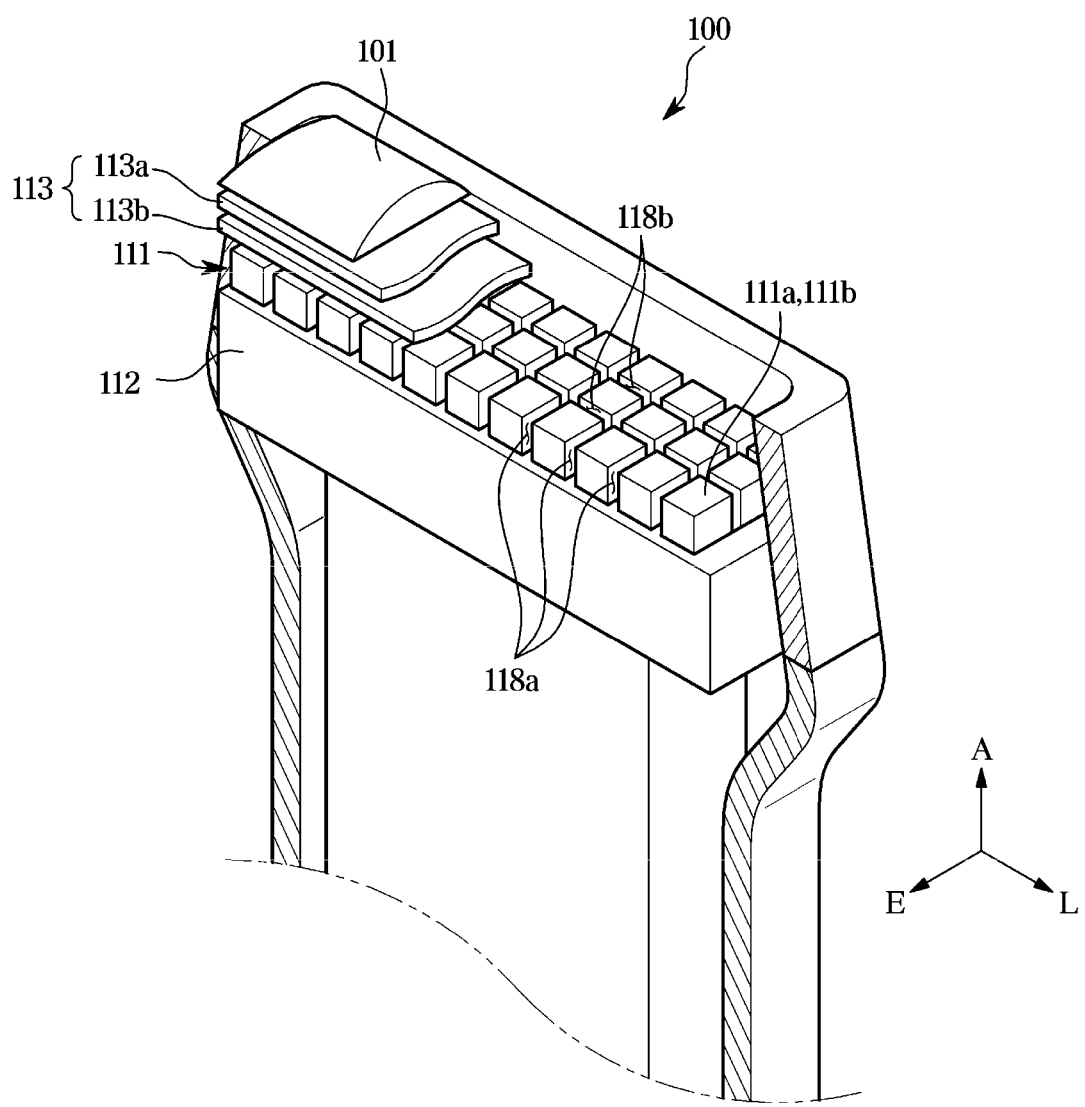
FIG. 3 is a perspective view illustrating a schematic structure of the ultrasonic probe according to an embodiment.

FIG. 3 is a perspective view illustrating a schematic structure of the ultrasonic probe according to an embodiment.

Referring to FIG. 3, the ultrasonic probe 100 according to an embodiment includes a piezoelectric layer 111, a sound absorbing layer 112 disposed below the piezoelectric layer 111, a matching layer 113 disposed above the piezoelectric layer 111, and a lens layer 101 disposed above the matching layer 113. The ultrasonic probe 100 also includes one or more kerfs 118a and 118b formed in the piezoelectric layer 111 to divide the piezoelectric layer 111 into a plurality of piezoelectric elements 111a and 111b.

In this case, the kerfs 118a and 118b refer to spaces formed by a dicing process in which the piezoelectric layer 111 is divided into the plurality of piezoelectric elements 111a and 111b.

Figure 8:
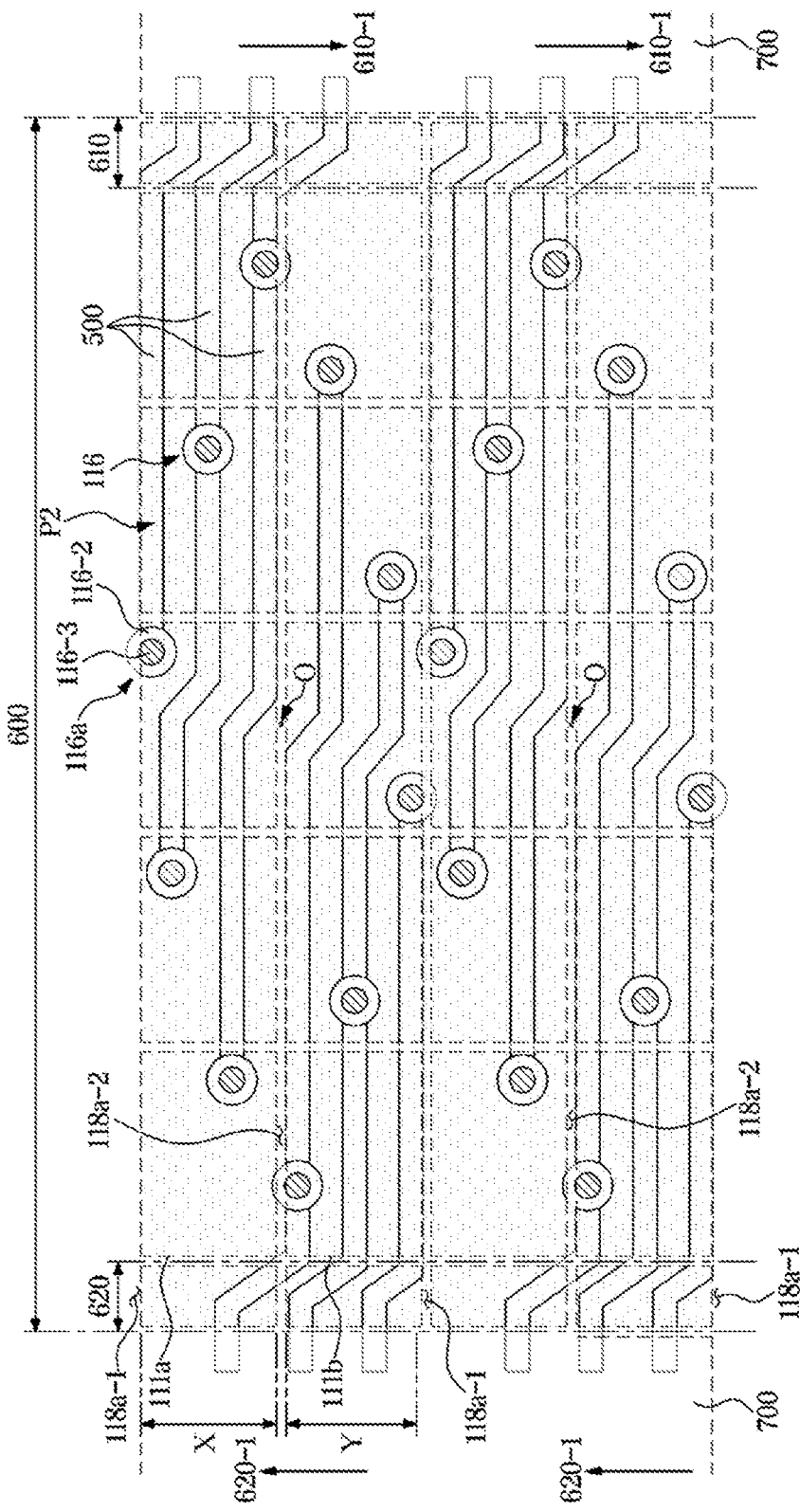
FIGS. 8 and 9 are views illustrating the interior of the ultrasonic probe according to an embodiment as viewed from the axis direction.

As illustrated in FIG. 8, the first kerfs 118a may be formed between the plurality of piezoelectric elements 111a and 111b along the lateral direction L of the ultrasonic probe 100. The second kerf 118b may be formed between the plurality of piezoelectric elements 111a and 111b along the elevation direction E of the transducer module 110. In the following description, the kerf is generally defined as referring to the first ken 118a.

When the second kerf 118b is formed between the plurality of piezoelectric elements 111a and 111b along the elevation direction E of the ultrasonic probe 100, the ultrasonic probe 100 may form a plurality of rows and form a multi-row array arrangement.

When the first kerfs 118a are formed between the plurality of piezoelectric elements 111a and 111b along the lateral direction L of the ultrasonic probe 100 and the second kerf 118b is formed between the plurality of piezoelectric elements 111a and 111b along the elevation direction E of the ultrasonic probe 100, as described above with reference to FIG. 2, the ultrasonic probe 100 may form a multidimensional transducer array arrangement and form a two-dimensional M×N matrix arrangement.

In addition, each cross section of the ultrasonic probe 100 may be described based on three directions forming a right angle with respect to the inner center of the ultrasonic probe 100.

Figure 4:
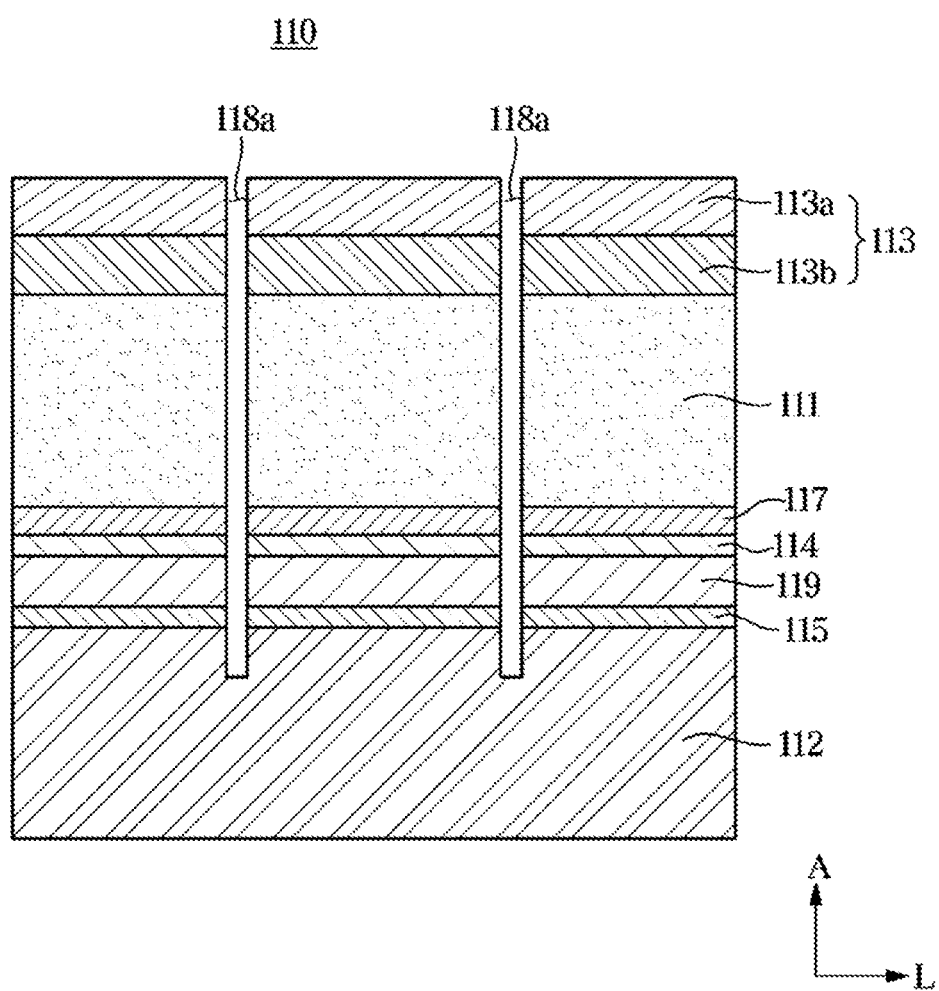
FIG. 4 is a cross-sectional view of a plane of the ultrasonic probe according to an embodiment along an axis direction and a lateral direction.
Figure 5:
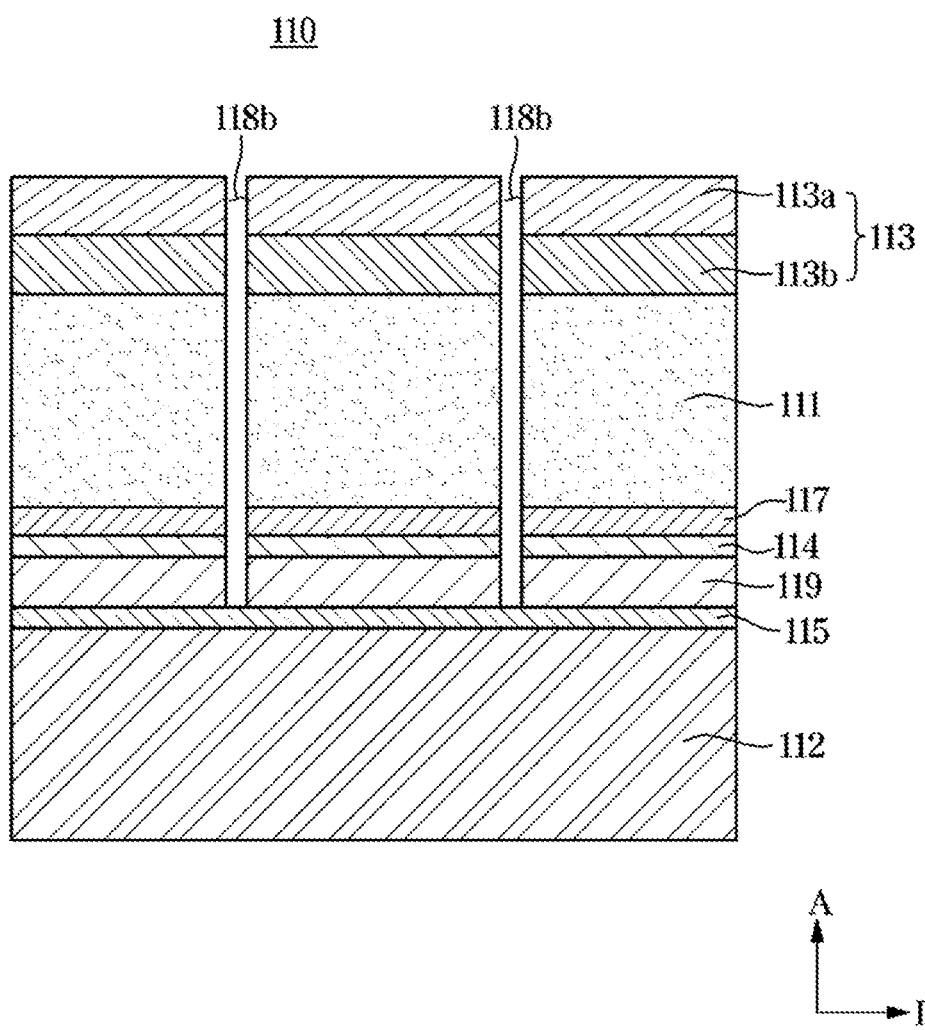
FIG. 5 is a cross-sectional view of a plane of the ultrasonic probe according to an embodiment along the axis direction and an elevation direction.

FIG. 4 is a cross-sectional view of a plane of the ultrasonic probe according to an embodiment along the axis direction and the lateral direction, and FIG. 5 is a cross-sectional view of a plane of the ultrasonic probe according to an embodiment along the axis direction and the elevation direction.

Referring to FIGS. 4 and 5, the ultrasonic transducer module 110 according to an embodiment includes the piezoelectric layer 111, the sound absorbing layer 112 disposed below the piezoelectric layer 111, and the matching layer 113 disposed above the piezoelectric layer 111.

The piezoelectric layer 111 is made of a piezoelectric body (piezoelectric material) that converts an electrical signal into mechanical vibration when the electrical signal is applied to generate ultrasonic waves. The piezoelectric body may be laminated in a single layer or multilayer structure.

Effects of generating a voltage when a mechanical pressure is applied to a predetermined material and causing a mechanical deformation when a voltage is applied are referred to as a piezoelectric effect and an inverse piezoelectric effect, respectively, and a material having these effects is referred to as a piezoelectric body (piezoelectric material).

That is, a piezoelectric body (piezoelectric material) is referred to as a material that converts electrical energy into mechanical vibration energy and mechanical vibration energy into electrical energy.

The piezoelectric body (piezoelectric material) may include a ceramic of lead zirconate titanate (PZT), a PZNT single crystal made of a solid solution of lead magnesium niobate and lead titanate, and the like. The piezoelectric layer 111 may also irradiate mechanical vibration energy as ultrasonic waves in a direction (hereinafter 'front') in which a lens is provided and a direction (hereinafter 'rear') in which the sound absorbing layer 112 is provided.

The piezoelectric layer 111 may be processed into a multidimensional array of a matrix form forming a plurality of rows by the dicing process. In this case, the piezoelectric layer 111 may be divided into the plurality of piezoelectric elements 111a by the kerfs 118a and 118b.

The sound absorbing layer 112 is provided below the piezoelectric layer 111 and absorbs ultrasonic waves generated in the piezoelectric layer 111 and traveling backward, thereby blocking the ultrasonic waves from propagating to the rear of the piezoelectric layer 111. Accordingly, the sound absorbing layer 112 may prevent distortion of an image. Also, the sound absorbing layer 112 may have an acoustic impedance smaller than that of the piezoelectric layer 111. For example, the sound absorbing layer 112 may be made of a material having an acoustic impedance of 2MRay1 to 5MRay1. Also, the sound absorbing layer 112 may be formed of a plurality of layers in order to improve the attenuation or blocking effect of ultrasonic waves.

The matching layer 113 is provided above the piezoelectric layer 111. The matching layer 113 may include a first matching layer 113a and a second matching layer 113b. The first and second matching layers 113a and 113b are layers that transmit ultrasonic waves to an object or reduce loss of ultrasonic waves transmitted from the object by properly matching the acoustic impedance of the piezoelectric layer 111 with the acoustic impedance of the object. The acoustic impedances of the object and the piezoelectric layer 111 may be matched by adjusting physical parameters such as sound speeds, thicknesses, and acoustic impedances of the first matching layer 113a and the second matching layer 113b. That is, the first matching layer 113a and the second matching layer 113b suppresses reflection of ultrasonic waves caused by a difference between the acoustic impedance of the object and the acoustic impedance of the piezoelectric layer 111. FIG. 5 illustrates the matching layers formed of two layers, but may not be limited thereto. Instead of the first and second matching layers 113a and 113b, matching layers formed of one or three or more layers may be used. The first and second matching layers 113a and 113b may be separated into a plurality of elements and may be provided on the top of the piezoelectric layer 111.

The matching layer 113 reduces the difference in acoustic impedance between the piezoelectric layer 111 and the object ob to match the acoustic impedances of the piezoelectric layer 111 and the object ob, so that ultrasonic waves generated in the piezoelectric layer 111 are efficiently transmitted to the object ob.

To this end, the matching layer 113 may be formed of a material having an acoustic impedance smaller than the piezoelectric layer 111 and larger than that of the object ob.

The matching layer 113 may be formed of a glass or resin material.

In addition, a plurality of the matching layers 113 may be provided so that the acoustic impedance may change stepwise from the piezoelectric layer 111 toward the object ob, and materials of the plurality of matching layers 113 may be different from each other.

Like the piezoelectric layer 111, the matching layer 113 may be processed in a multidimensional array of a matrix form by the dicing process and may be processed into a one-dimensional array form.

The lens layer 101 may be provided to cover the top of the matching layer 113. The lens layer 101 focuses ultrasonic waves traveling forward of the layers of transducer module 110 to a specific point.

The lens layer 101 may be formed of a material having strong wear resistance and high ultrasonic propagation speed in order to focus ultrasonic waves and protect the acoustic module, in particular, the piezoelectric layer 111. The lens layer 101 may have a convex shape in the direction of ultrasonic radiation to focus ultrasonic waves and may be implemented in a concave shape when the sound velocity is slower than the object ob.

In the disclosed embodiment, a case in which one of the lens layer 101 is formed below the matching layer 113 is described as an example, but a plurality of the lens layers 101 having different physical properties may be formed.

The ultrasonic transducer module 110 according to an embodiment may further include a first circuit layer 114 and a second circuit layer 115 disposed between the piezoelectric layer 111 and the sound absorbing layer 112.

The first circuit layer 114 and the second circuit layer 115 may include electrodes to which an electrical signal may be applied. In this case, the first circuit layer 114 and the second circuit layer 115 may include at least one of a signal electrode (not shown) receiving current and a ground electrode (not shown) emitting current.

To this end, at least one of the first circuit layer 114 and the second circuit layer 115 may be implemented as a printed circuit board (PCB).

In addition, at least one of the first circuit layer 114 and the second circuit layer 115 may be implemented as a flexible printed circuit board (FPCB).

The second circuit layer 115 may be formed to be spaced apart from the first circuit layer 114 and may be formed to be spaced apart based on a predetermined interval.

Various configurations may be disposed between the first circuit layer 114 and the second circuit layer 115. For example, an insulating layer 119 may be disposed between the first circuit layer 114 and the second circuit layer 115.

The insulating layer 119 may prevent the first circuit layer 114 and the second circuit layer 115 from being directly in contact with each other. To this end, the insulating layer 119 may be made of a non-conductive material.

For example, the insulating layer 119 may be formed using an epoxy resin. Because the epoxy resin may provide an adhesive function, the first circuit layer 114 and the second circuit layer 115 may be adhered to each other by the insulating layer 119 made of an epoxy resin.

The disclosed embodiment describes a case in which the insulating layer 119 is disposed between the first circuit layer 114 and the second circuit layer 115 as an example, but positions of the first circuit layer 114, the second circuit layer 115, and the insulating layer 119 are not limited to the above-described example, and may be disposed at various positions.

In addition, in addition to the insulating layer 119, one or more circuit layers may be disposed between the first circuit layer 114 and the second circuit layer 115.

Electrodes may be formed at the top and bottom of the piezoelectric layer 111 so that an electrical signal transmitted from the first circuit layer 114 is transmitted to the piezoelectric layer 111. The electrodes formed at the top and bottom may be provided as ceramic electrodes.

The electrodes may be formed in a round type method (see FIGS. 12 and 13) provided with a lower electrode of the piezoelectric body 111 electrically connected to the first circuit layer 114 and an upper electrode of the piezoelectric layer 111 formed to surround the top of the piezoelectric layer 111 and side surfaces of the piezoelectric layer 111. In this case, the upper electrode may be electrically connected to a ground electrode (GND) provided on the PCB.

Alternatively, although not shown in the drawing, the upper electrode does not require the ground electrode (GND) provided on the PCB like the round type method described above, and may be formed in a one-step bonding type method (not shown) in which the upper electrode formed on the top of the piezoelectric layer 111 extends to form the ground electrode (GND).

The ultrasonic probe 100 according to an embodiment may further include an enhanced layer 117. The enhanced layer 117 may reflect ultrasonic waves generated from the piezoelectric layer 111. The enhanced layer 117 may be disposed below the piezoelectric layer 111 and above the first circuit layer 114, and may be formed in being directly in contact with or spaced apart from the piezoelectric layer 111. That is, the enhanced layer 117 may be disposed between the piezoelectric layer 111 and the first circuit layer 114 and may be provided such that an electrical signal transmitted from the first circuit layer 114 is transmitted to the piezoelectric layer 111. The enhanced layer 117 may be made of a conductive material.

The transducer module 110 may form the one or more kerfs 118a and 118b by the dicing process and may include the plurality of piezoelectric elements 111a.

As illustrated in FIG. 4, the transducer module 110 may include the first kerfs 118a formed between the piezoelectric elements 111a along the lateral direction L. The first kerfs 118a may be formed regularly at a predetermined interval. However, the first kerfs 118a are not limited thereto, and may be formed at different intervals.

M-th rows in a two-dimensional MXN matrix arrangement may be defined as pairs having two matrices. Hereinafter, a transducer element consisting of a pair of rows is defined as a base pair element. Details related to the base pair element will be described later.

In the case of the first kerf 118a, a depth of formation of the first kerf 118a may vary according to a formation position based on a transducer element formed of a pair of rows, which will be described later, that is, the base pair element.

The first kerfs 118a may be divided into a case where first kerfs 118a-1 (FIGS. 8 to 11) are formed between the base pair elements and a case where second kerfs 118a-2 (FIGS. 8 to 11) are formed between two rows of the base pair element to be formed in different forms.

In the case where the first kerfs 118a-1 are formed between the base pair elements, the first kerfs 118a-1 may be formed to separate at least one of the matching layer 113, the enhanced layer 117, the first circuit layer 114, the second circuit layer 115 and the insulating layer 119, as well as the piezoelectric layer 111.

When the kerfs 118a and 118b are formed to have a width smaller than a diameter of the connection part 116, the kerfs 118a and 118b may penetrate the connection part 116. Accordingly, when the first kerf 118b-1 is formed between the base pair elements, the first kerf 118b-1 may be formed to separate the second circuit layer 115 because there is no risk of the first circuit layer 115 being disconnected.

To this end, the first kerf 118a-1 may be formed to extend from a top surface of the piezoelectric element 111a to a specific position of any one of the matching layer 113, the enhanced layer 117, the first circuit layer 114, the second circuit layer 115 and the insulating layer 119.

In the case where the second kerf 118a-2 (FIGS. 8 to 11) are formed between two rows of the base pair element, the second kerf 118a-2 may be formed to separate at least one of the matching layer 113, the enhanced layer 117, the first circuit layer 114, and the insulating layer 119, as well as the piezoelectric layer 111. That is, the second kerf 118a-2 may not be formed on the second circuit layer 115.

As illustrated in FIG. 5, the transducer module 110 may include the second kerfs 118b formed between the piezoelectric elements along the elevation direction E. The second kerfs 118b may be formed regularly at a predetermined interval. However, the second kerfs 118b are not limited thereto, and may be formed at different intervals.

In this case, the second kerf 118b may be formed to separate at least one of the matching layer 113, the enhanced layer 117, the first circuit layer 114, and the insulating layer 119, as well as the piezoelectric layer 111. To this end, the second kerf 118b may be formed to extend from the top surface of the piezoelectric element 111a to a specific position of any one of the matching layer 113, the enhanced layer 117, the first circuit layer 114, and the insulating layer 119. In this case, the second kerf 118b may prevent electrical disconnection of the second circuit layer 115 because the second kerf 118b may not be formed to penetrate the second circuit layer 115.

Figure 6:
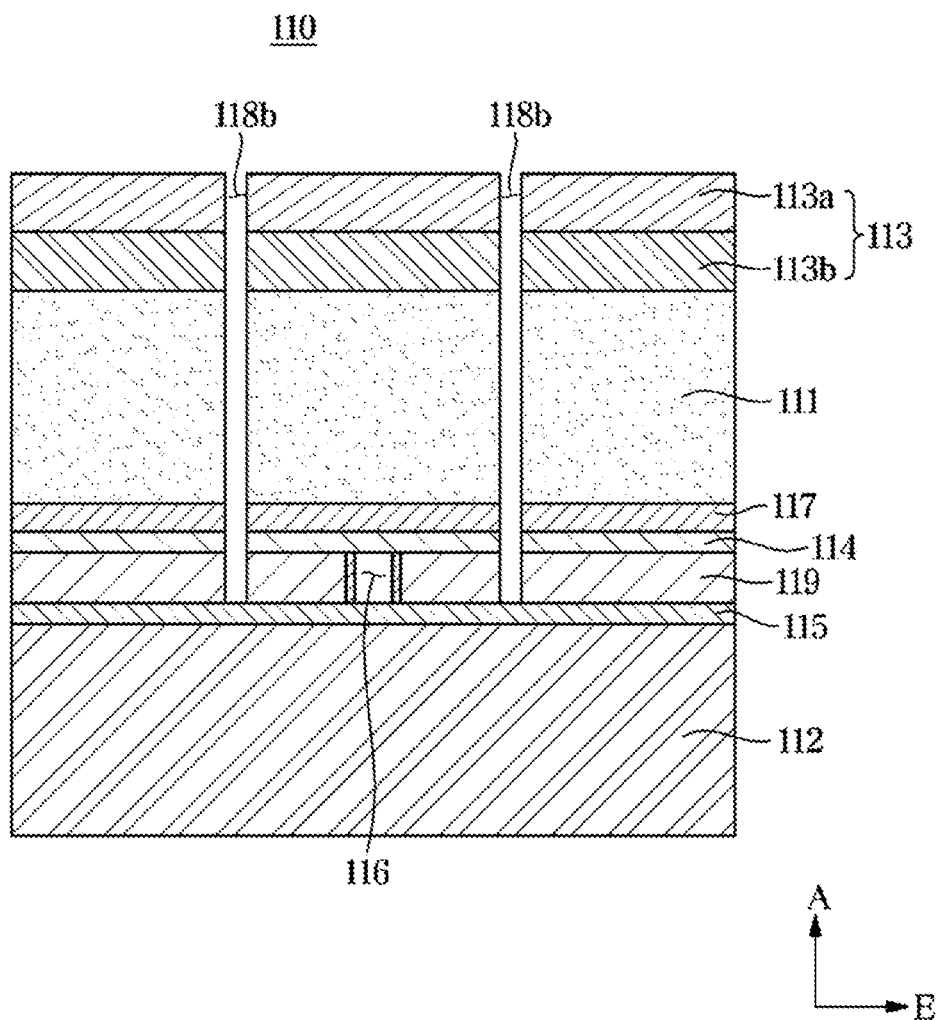
FIG. 6 is a view for explaining an arrangement relationship between a first circuit layer and a second circuit layer of a first connection part according to an embodiment.
Figure 7:
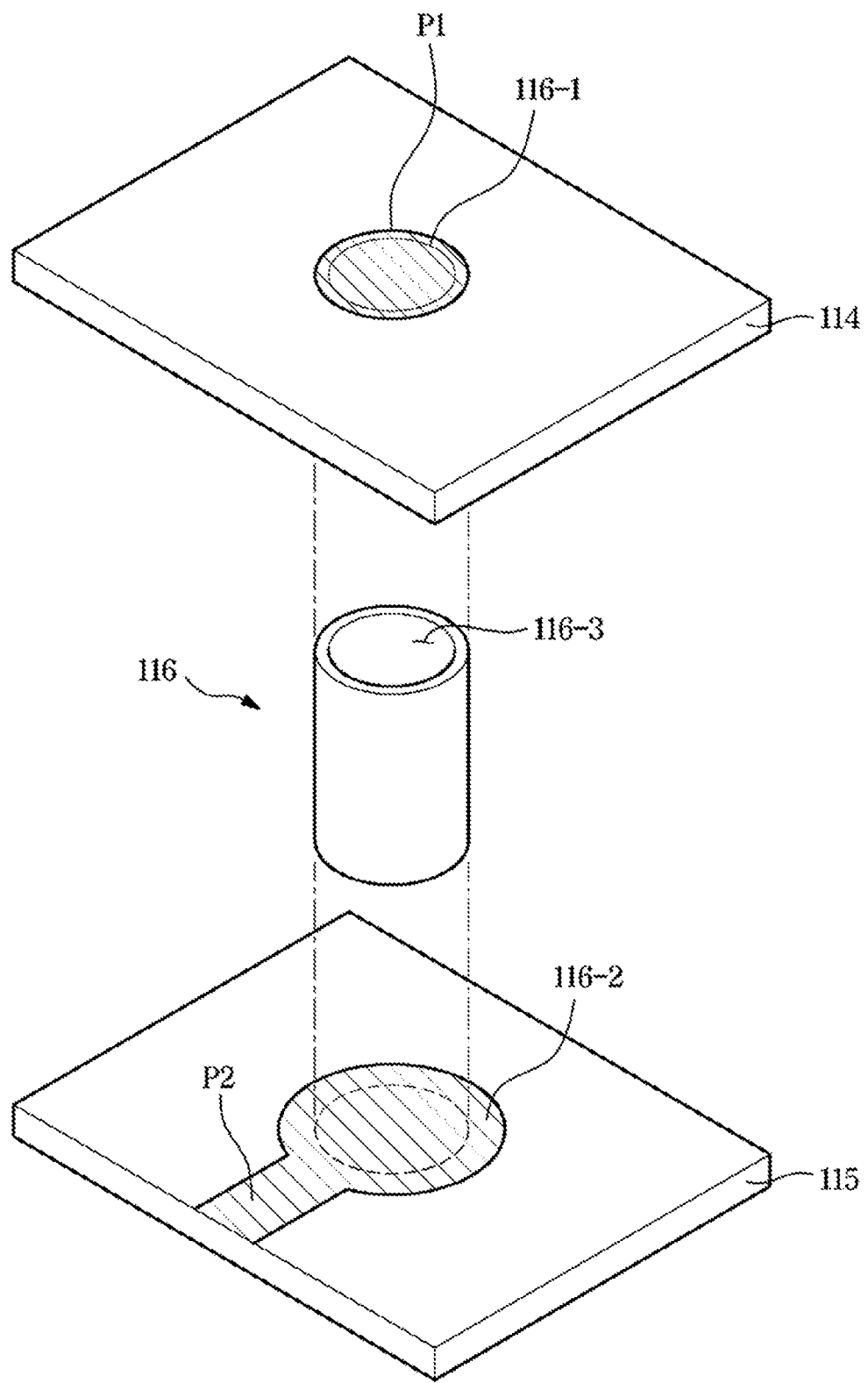
FIG. 7 is a view for explaining the first connection part and a second connection part according to an embodiment.

FIG. 6 is a view for explaining an arrangement relationship between a first circuit layer and a second circuit layer of a first connection part according to an embodiment, and FIG. 7 is a view for explaining the first connection part and a second connection part according to an embodiment.

The connection part 116 according to an embodiment of the disclosure may include a first connection part 116a and a second connection part 116b (see FIGS. 8 to 11). The first connection part 116a and the second connection part 116b electrically connect each layer in the same manner. Hereinafter, description will be made based on the first connection part 116a connecting the first circuit layer 114 and the second circuit layer 115 illustrated in FIGS. 6 and 7.

Referring to FIGS. 6 and 7, the ultrasonic probe 100 according to an embodiment includes the piezoelectric layer 111, the sound absorbing layer 112 disposed below the piezoelectric layer 111, the matching layer 113 disposed above the piezoelectric layer 111, the circuit first layer 114, and the second circuit layer 115, the enhanced layer 117, the insulating layer 119, and the second kerf 118b formed between the piezoelectric elements along the elevation direction E, and further includes the connection part 116 connecting the first circuit layer 114 and the second circuit layer 115.

The connection part 116 may include a via hole 116-3. The connection part 116 may be formed by a process for forming the via hole 116-3, and the via hole 116-3 may be formed in various processes including a laser via drilling process or an etching process.

The connection part 116 may electrically connect the first circuit layer 114 and the second circuit layer 115 by at least one of conductive paste, conductive plating, sputtering, and printing. However, the disclosure is not limited to the above-described example, and the first circuit layer 114 and the second circuit layer 115 may be electrically connected by various connection methods. In this case, the via hole 116-3 may be implemented as a conductive hole. For example, the via hole 116-3 may be implemented as a conductive hole formed by being plated or processed with a conductive material such as gold, silver, and copper, but is not limited to the above-described example.

The connection part 116 may be formed to extend from the first circuit layer 114 to the second circuit layer 115. The connection part 116 may be formed to penetrate the first circuit layer 114 and the second circuit layer 115. In this case, the via hole 116-3 may be implemented in the form of a through-hole.

The connection part 116 may also be formed to penetrate only one of the first circuit layer 114 and the second circuit layer 115. In this case, the via hole 116-3 may be implemented in the form of a blind-hole.

The connection part 116 may also be formed such that the inside of the via hole is filled with a predetermined amount of a conductive material. In this case, the via hole 116-3 may be implemented in the form of a filled-via.

As illustrated in FIG. 7, the connection part 116 may be formed to connect circuit patterns P1 and P2 composed of conductive wires formed on the first circuit layer 114 and the second circuit layer 115. As will be described later, each of the circuit patterns P1 and P2 may include a plurality of wires. Therefore, connecting the circuit patterns P1 and P2 means connecting each wire. The connection part 116 may include the via hole 116-3 connecting the first circuit layer 114 and the second circuit layer 115.

The connection part 116 may electrically connect the first circuit layer 114 and the second circuit layer 115. To this end, the connection part 116 may be in contact with the first circuit layer 114 and the second circuit layer 115 at opposite ends thereof.

Specifically, the connection part 116 may be in contact with the first circuit layer 114 and the second circuit layer 115 at the opposite ends thereof by being connected to the first circuit pattern P1 formed on the first circuit layer 114 and the second circuit pattern P2 formed on the second circuit layer 115. That is, the connection part 116 may be connected to both ends of the wire of the first circuit pattern P1 and the wire of the second circuit pattern P2 formed on the second circuit layer 115 corresponding thereto.

In this case, each of the first circuit pattern P1 and the second circuit pattern P2 may include an electrode and may be implemented as a conductive material such as copper. In addition to the embodiment illustrated in FIG. 8, the first circuit pattern P1 and the second circuit pattern P2 may have various forms or shapes for wires.

The connection part 116 may include a first substrate connection part 116-1 located on the first circuit pattern P1 and a second substrate connection part 116-2 located on the second circuit pattern P2. The connection part 116 may be in contact with the first circuit layer 114 through the first substrate connection part 116-1 and may be in contact with the second circuit layer 115 through the second substrate connection part 116-2.

The first substrate connection part 116-1 may be formed to have the same size as the via hole 116-3. However, the first substrate connection part 116-1 is not limited thereto, and may be formed to have a size larger or smaller than the via hole 116-3.

The first substrate connection part 116-1 may have a circular shape when viewed from a vertical upper direction of the first circuit layer 114. Depending on the embodiment, the first substrate connection part 116-1 may have a polygonal shape such as a triangle and a square, or may have a shape such as an ellipse. The first substrate connection part 116-1 may be formed on the first circuit layer 114 by perforating the first circuit layer 114 using a perforating device such as a drill tool.

The second substrate connection part 116-2 may be formed to have a larger size than the via hole 116-3. That is, a diameter of the second substrate connection part 116-2 may be larger than a diameter of the via hole 116-3. In this case, when the first substrate connection part 116-1 has the same size as the via hole 116-3, the second substrate connection part 116-2 may have a diameter larger than a diameter of the first substrate connection part 116-1. However, the size of the second substrate connection part 116-2 is not limited to the above-described example, and may be formed to have the same size as the via hole 116-3, or may be formed to have a smaller size than the via hole 116-3.

The second substrate connection part 116-2 may have a circular shape when viewed from a vertical upper direction of the second circuit layer 115. Depending on the embodiment, the second substrate connection part 116-2 may have a polygonal shape such as a triangle and a square, or may have a shape such as an ellipse. The second substrate connection part 116-2 may be formed on the second circuit layer 115 by perforating the second circuit layer 115 using a perforating device such as a drill tool.

Figure 9:
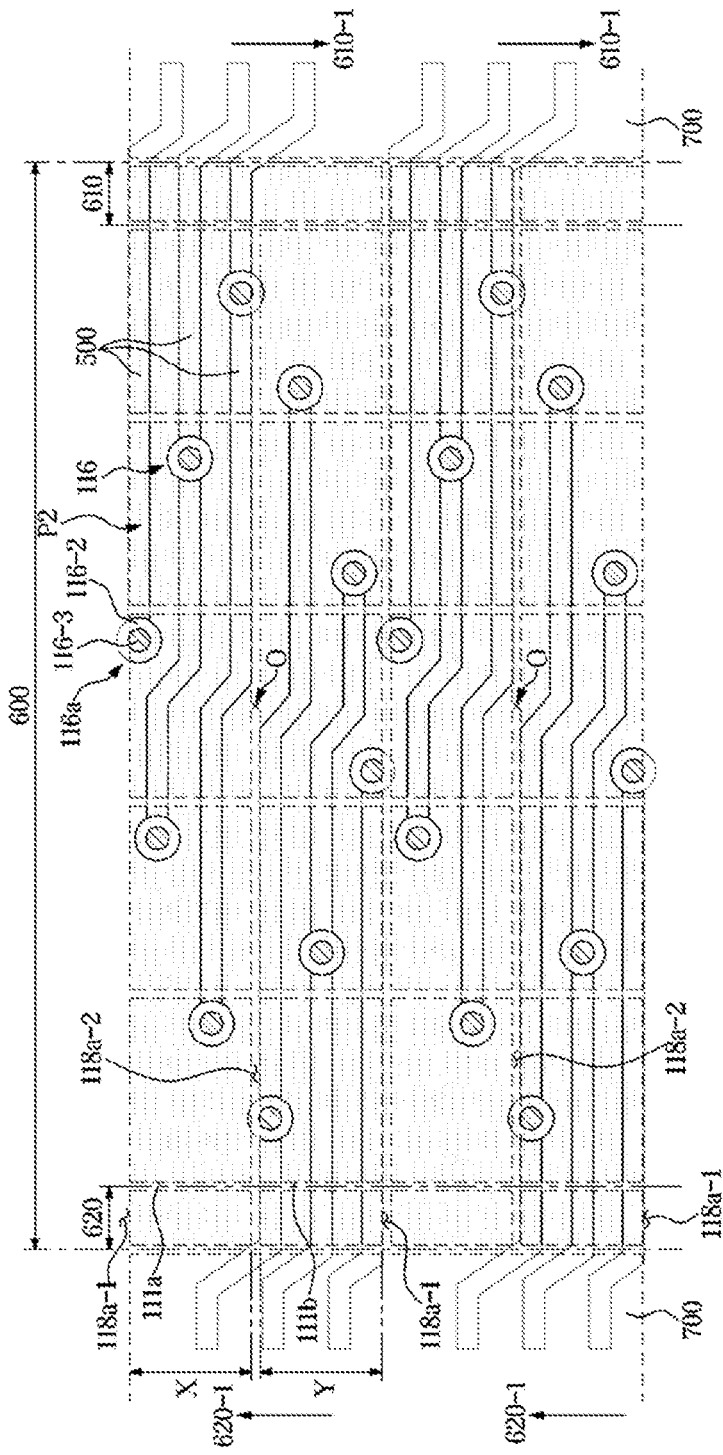
Figure 10:
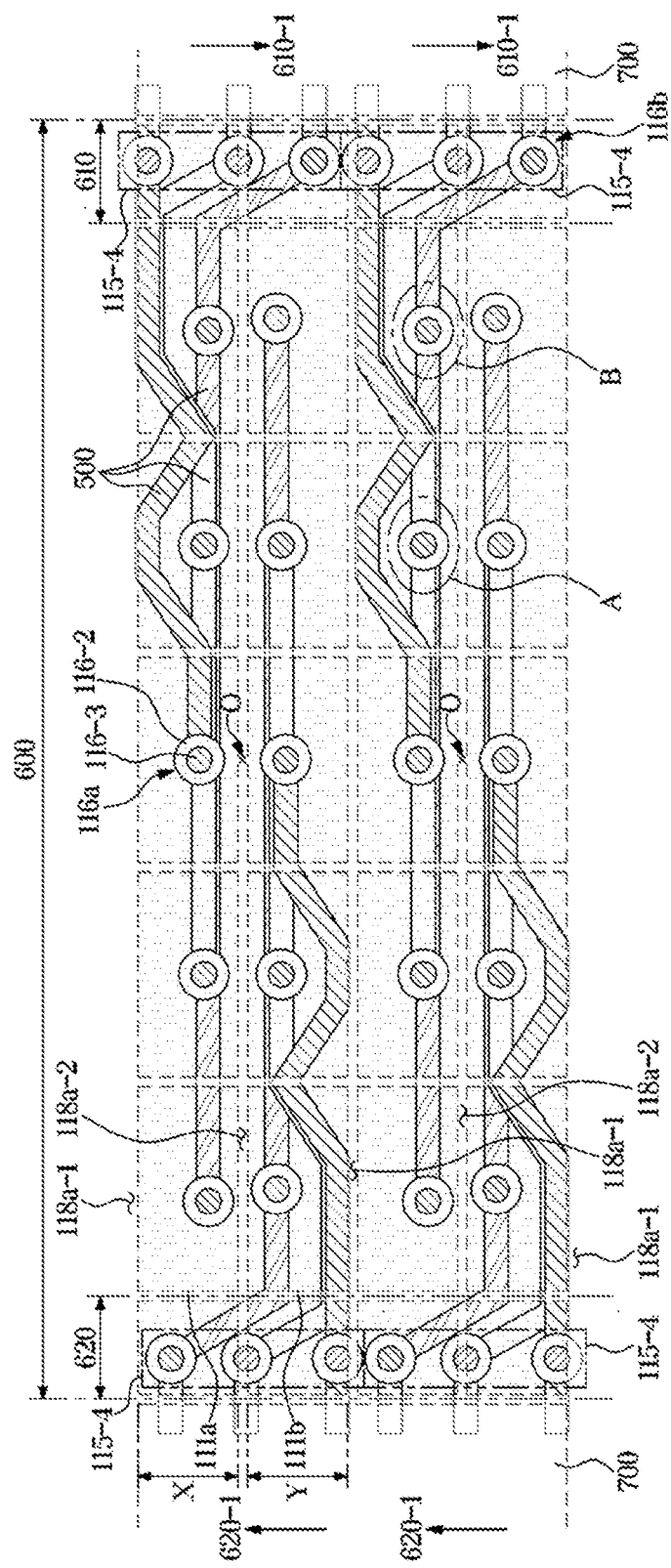
FIGS. 10 and 11 are views illustrating the interior of an ultrasonic probe according to another embodiment as viewed from the axis direction.
Figure 11:
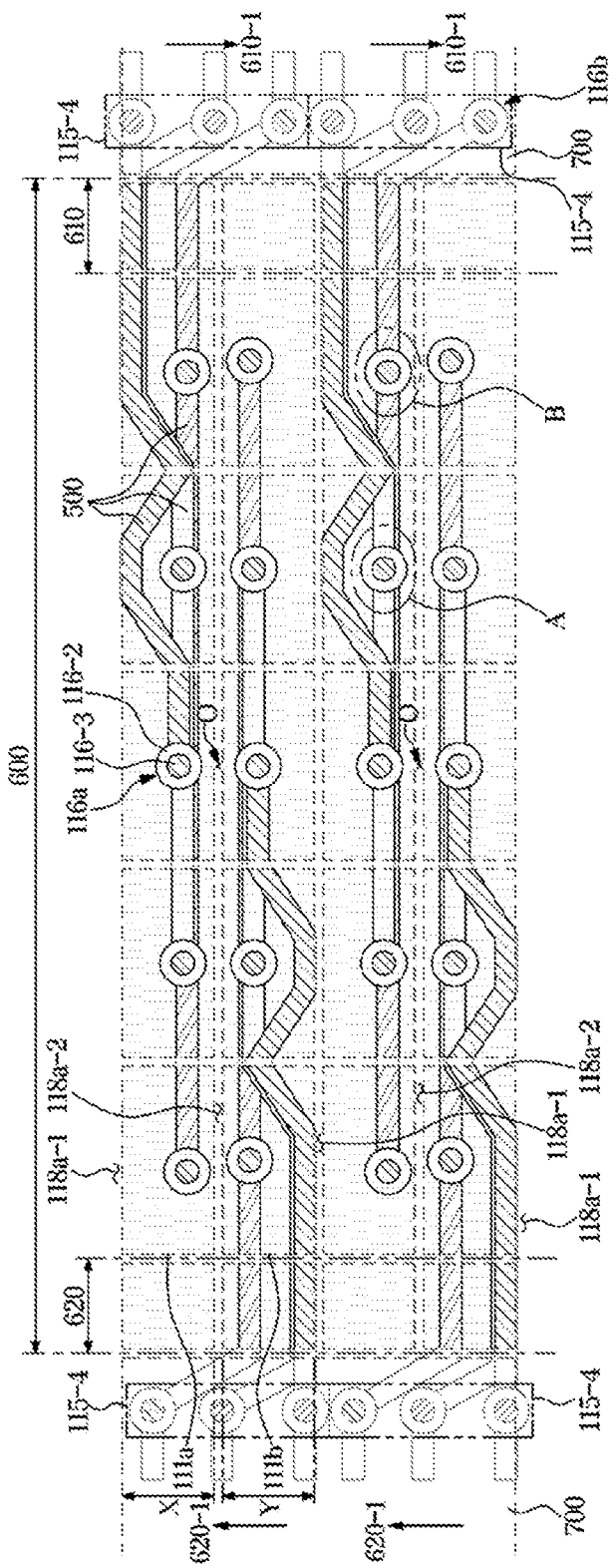
Figure 12:
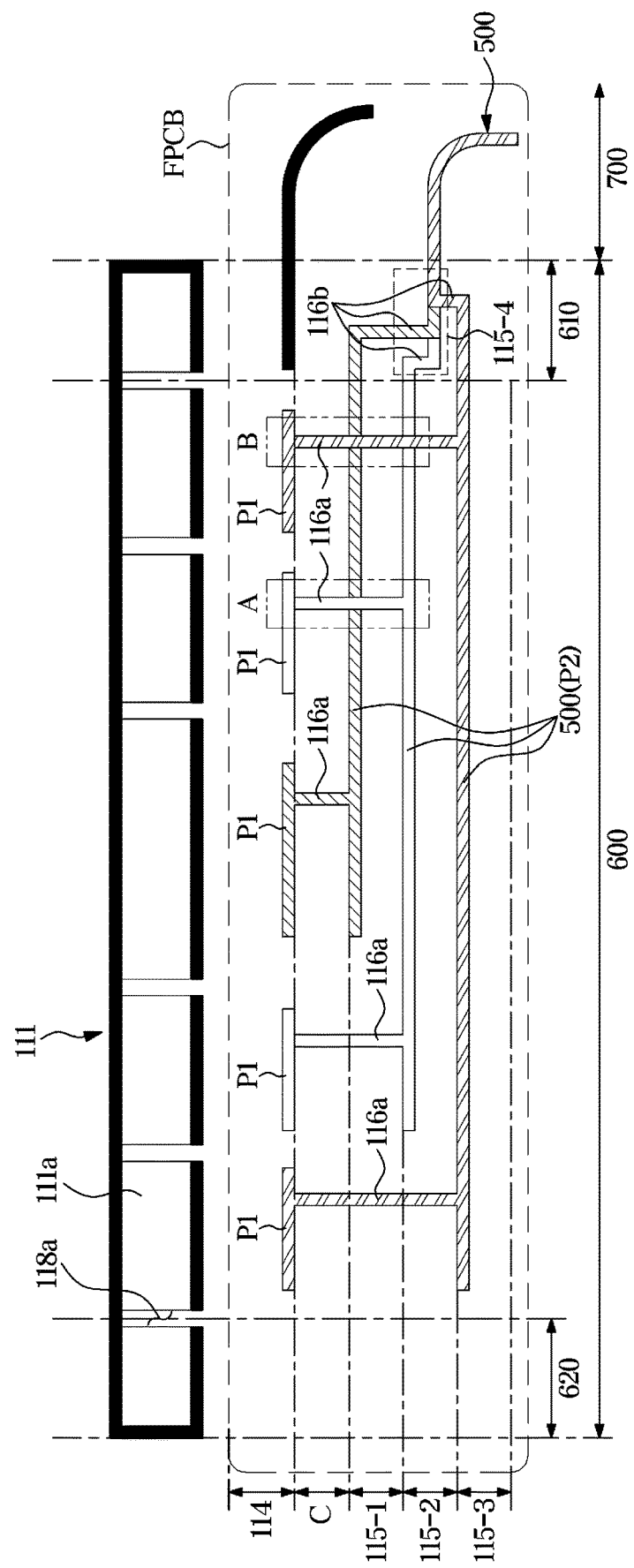
FIGS. 12 and 13 are views schematically illustrating cross-sections of an odd element X of the ultrasonic probe according to FIGS. 10 and 11, respectively.
Figure 13:
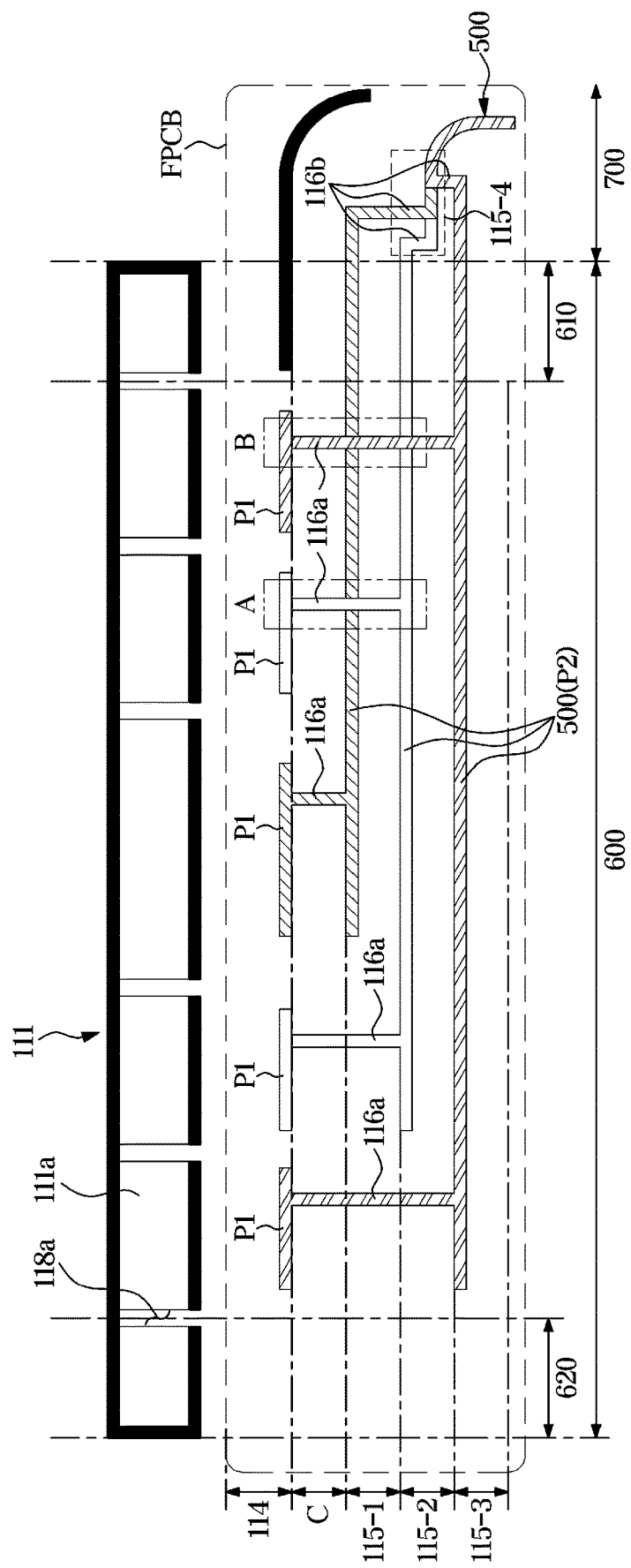

FIGS. 8 and 9 are views illustrating the interior of the ultrasonic probe according to an embodiment as viewed from the axis direction, FIGS. 10 and 11 are views illustrating the interior of an ultrasonic probe according to another embodiment as viewed from the axis direction, and FIGS. 12 and 13 are views schematically illustrating cross-sections of an odd element X of the ultrasonic probe according to FIGS. 10 and 11, respectively. Hereinafter, the plurality of piezoelectric elements 111a and 111b formed in a two-dimensional MXN matrix arrangement will be described in detail.

As described above, when the first kerfs 118a are formed between the plurality of piezoelectric elements 111a and 111b along the lateral direction L of the ultrasonic probe 100 and the second kerfs 118b are formed between the plurality of piezoelectric elements 111a and 111b along the elevation direction E of the ultrasonic probe 100, as described above with reference to FIG. 2, the ultrasonic probe 100 may form a multidimensional transducer array arrangement and may form a two-dimensional M×N matrix arrangement. Hereinafter, one of the M-th rows is defined as a transducer element.

The M-th rows in the two-dimensional MXN matrix arrangement may be defined as pairs having two matrices. Hereinafter, a transducer element consisting of a pair of rows is defined as a base pair element. Also, a transducer element in one row of the base pair elements is defined as an odd element X, and a transducer element in the other row is defined as an even element Y.

Referring to FIGS. 8 to 11, the first kerf 118a and the second kerf 118b are formed between a plurality of piezoelectric elements (described as 111a and 111b for convenience) along the lateral direction L in the ultrasonic probe 100 according to an embodiment of the disclosure.

The plurality of piezoelectric elements 111a and 111b may be arranged on a multidimensional transducer array arrangement, that is, a two-dimensional MXN matrix arrangement. Accordingly, the plurality of piezoelectric elements may be defined according to the base pair element, the odd element X, and the even element Y defined above.

The plurality of piezoelectric elements 111a included in the odd element X may be defined as the odd row piezoelectric element 111a, and the plurality of piezoelectric elements 111b included in the even element Y may be defined as the even row piezoelectric element 111b.

Hereinafter, the second circuit layer 115 electrically connected to the plurality of piezoelectric elements 111a and 111b will be described in detail with reference to FIGS. 8 to 11.

Referring to FIG. 8, the second circuit layer 115 may be disposed at lower ends of the plurality of piezoelectric elements 111a and 111b indicated by dotted lines. Specifically, as illustrated in FIGS. 4 to 6, the second circuit layer 115 may be provided below the first circuit layer 114 to be spaced apart from each other. The insulating layer 119 may be additionally provided between the first circuit layer 114 and the second circuit layer 115. However, in describing FIGS. 8 and 11 illustrating the interior of the ultrasonic probe 100 viewed from the axis direction, descriptions of configurations other than the plurality of piezoelectric elements 111a and 111b, the second circuit layer 115, and the connection part 116 will be omitted.

In addition, in describing FIGS. 12 and 13, descriptions of configurations other than the plurality of piezoelectric elements 111a, the first circuit layer 114, the second circuit layer 115, and the connection part 116 will be omitted (see reference numeral C in FIGS. 12 and 13).

Referring to FIGS. 8 to 11, a plurality of circuit patterns may be formed on the second circuit layer 115. The circuit patterns may include the second circuit pattern P2 formed on the second circuit layer 115 described above. The second circuit pattern P2 may include a plurality of wires. A specific structure of the plurality of wires will be described later.

The second circuit layer 115 may be divided into a first region 600 and a second region 700.

The first region 600 may be provided to be selectively in contact with the plurality of piezoelectric elements 111a and 111b. That is, the first region 600 may be defined as a region in which electrical energy is converted into mechanical vibration energy and mechanical vibration energy is converted into electrical energy.

When viewed from a vertical upper direction of the piezoelectric elements 111a and 111b, the first region 600 of the second circuit layer 115 may be formed on the second substrate connection part 116-2 through which the via hole 116-3 of the connection part 116 is connected to the second pattern P2 of the second circuit layer 115.

The second pattern P2 of the second circuit layer 115 may be formed to have various shapes and may be formed to have a wiring structure for at least one piezoelectric element through the via hole 116-3.

Hereinafter, a specific shape of the second circuit pattern P2 formed in the first region 600 of the second circuit layer 115 will be described.

As illustrated in FIGS. 8 and 11, when the transducer module 110 forms an ultrasonic 5×4 array in an E-L plane, the second pattern P2 may be formed to connect piezoelectric elements positioned in second and fourth columns and connect piezoelectric elements positioned in first and fifth columns, and the piezoelectric elements positioned in a third column may be formed to have separate wirings. When the transducer module 110 forms an ultrasonic 5×4 array in the E-L plane in the above manner, three wires may be formed in a single row of transducer elements. However, the second pattern P2 is not limited to the 5×4 arrangement, and may be variously modified according to the design specifications as an M×N arrangement, and accordingly, the wiring structure for the piezoelectric elements is also not limited to three wires, and may be changed into various numbers of wires.

As illustrated in FIG. 8, in forming the second pattern P2 on the second circuit layer 115 of the ultrasonic probe 100 according to an embodiment of the disclosure, a plurality of wires 500 is provided to be formed on a single layer. Herein, being formed in a single layer means that the plurality of wires 500 of the second pattern P2 are formed in one layer based on the axis direction A. Accordingly, the plurality of wires 500 may be formed in parallel on a single layer, that is, on the same surface along an extending direction of the odd element X or the even element Y.

Or as a method in which the plurality of wires 500 is arranged in parallel, as illustrated in FIG. 8, by forming a curved section in the wiring, the connection part 116 may be efficiently disposed and a width of the transducer element in one row may be reduced.

Or as illustrated in FIGS. 10 and 13, according to another embodiment of the disclosure, the second circuit layer 115 may include a plurality of sub-circuit layers 115-1, 2, and 3 laminated in the axial direction A. In forming the second pattern P2 on the second circuit layer 115 of the ultrasonic probe 100, each of the plurality of wires 500 may be formed in each of the plurality of sub-circuit layers 115-1, 2, and 3.

For example, when the transducer module 110 forms an ultrasonic 5×4 array in the E-L plane, three wires need to be formed in the second circuit layer 115 corresponding to the transducer element formed in one row. Accordingly, in order to form three wires, the second circuit layer 115 may include three of the sub-circuit layers 115-1, 2 and 3 (see FIGS. 12 and 13).

The plurality of wires 500 formed on each of the plurality of sub-circuit layers 115-1, 2, and 3 may be connected to the second circuit layer 115 through the first connection part 116a. Because the plurality of wires 500 is formed in a plurality of layers based on the axis direction A, heights of the first connection parts 116a disposed on the respective wires may be different from each other.

Specifically, the height of the first connection part 116a connecting the first circuit layer 114 and the sub-circuit layer 115-1 located closest to the first circuit layer 114 may be the lowest, and the height of the first connection part 116a connecting the first circuit layer 114 and the sub-circuit layer 115-3 located furthest to the first circuit layer 114 may be the highest.

Referring to FIGS. 10 to 13, in forming the second pattern P2 on the second circuit layer 115, by forming each of the plurality of wires 500 on each of the plurality of sub-circuit layers 115-1, 2, and 3 through the above-described first connection parts 116a, unlike the case where the plurality of wires 500 is formed on a single layer, the plurality of wires 500 may be formed to overlap in the axis direction A.

In other words, as illustrated in FIGS. 10 to 13, a plurality of wires 500 may be formed to overlap in a vertical direction based on the internal shape of the ultrasonic probe 100 viewed from the axis direction A. Because the first connection parts 116a is provided such that the plurality of wires 500 overlaps in the vertical direction, bypass regions A and B may be required.

For example, when the transducer module 110 forms an ultrasonic 5×4 array in the E-L plane, in the second circuit layer 115 corresponding to the transducer element consisting of one row, three wires are required, and three of the sub-circuit layers 115-1, 2, and 3 (see FIG. 11) may be provided. In this case, the bypass regions A and B for the remaining first connection parts 116a except for the first connection part 116a connecting the sub-circuit layer 115-1 located closest to the second circuit layer 115 and the second circuit layer 115 may be required.

Therefore, as illustrated in FIG. 10, each of the plurality of wires 500 formed on the remaining circuit layers except for the sub-circuit layer 115-3 located farthest from the second circuit layer 115 may be formed to overlap in the axis direction A and at the same time, may be formed to bypass the first connection part 116a of the wire located in a relatively lower layer. The bypass shape of the wiring may be formed in a shape of maintaining a straight line and being bent as illustrated in FIG. 10, but is not limited thereto, and may be formed in various shapes including curves.

The second region 700 of the second circuit layer 115 may be disposed at opposite ends of the first region 600 of the second circuit layer 115. The second region 700 of the second circuit layer 115 may be defined as an intermediate region in which the plurality of wires 500 in the first region 600 of the second circuit layer 115 and the cable 170 are connected.

That is, the second region 700 of the second circuit layer 115 is defined as an intermediate region in which the plurality of wires 500 in the first region 600 of the second circuit layer 115, which is provided to transmit a signal received from the piezoelectric layer 111 of the ultrasonic probe 100 to the system controller of the main body 200 or to transmit a control signal from the system controller to the piezoelectric layer 111 of the ultrasonic probe 100, and the cable 170 are connected.

A surface forming the transducer module 110 and an axis of the ultrasonic probe 100 may be provided to be substantially perpendicular (see FIG. 2). That is, the second circuit layer 115 disposed at the lower ends of the plurality of piezoelectric elements 111a and 111b and the axis of the ultrasonic probe 100 may also be provided to be substantially perpendicular.

Therefore, the second region 700 of the second circuit layer 115 may inevitably be folded toward a body of the ultrasonic probe 100 to which the cable 170 is connected in the manufacturing process of the ultrasonic probe 100.

In a conventional case of the multi-row ultrasonic probe 100, the plurality of wires 500 disposed on the transducer elements in one row may be configured not to deviate from rows through which the wires 500 extend when extending to the second region 700 of the second circuit layer 115. The odd element X or the even element Y may correspond to the transducer elements in one row.

In other words, the plurality of wires 500 disposed on the odd element X may be configured not to invade the row of the even element Y when extending to the second region 700 of the second circuit layer 115. Similarly, the plurality of wires 500 disposed on the even element Y may be configured not to invade the row of the odd element X when extending to the second region 700 of the second circuit layer 115.

In addition, when the plurality of wires 500 disposed on the hall element X are configured to extend to one side of the second region 700 of the second circuit layer 115, the plurality of wires 500 disposed on the even element Y may be configured to extend to the other side of the second region 700 of the second circuit layer 115. That is, the plurality of wires 500 provided on the first region 600 of the second circuit layer 115 may be provided to alternately extend through the second region 700 of the second circuit layer 115 along the row of the odd element X or the row of the even element Y.

According to the above-described structure, when the plurality of wires 500 of the second circuit pattern P2 is arranged on a single layer, restrictions in designing a pitch of the transducer element in one row may be caused due to the need for securing a thickness of the wire and a gap between the wires.

In addition, in forming the second pattern P2 on the second circuit layer 115 to solve the above problem when the plurality of wires 500 of the second circuit pattern P2 is arranged on a single layer, each of the plurality of wires 500 may be formed on each of the plurality of sub-circuit layers 115-1, 2 and 3.

That is, by forming each of the wires 500 in the plurality of sub-circuit layers 115-1, 2, and 3 of the second circuit layer 115 provided as different layers, the need for securing the thickness of the wire and the gap between the wires is reduced, so that the restrictions in designing the pitch of the transducer element in one row may be reduced (The transducer element in one row in FIG. 10 may be formed to have a narrower pitch than pitch the transducer element in one row in FIG. 8.).

However, even in the structure of the second circuit layer 115 having the plurality of sub-circuit layers 115-1, 2 and 3, when the wire formed in the second circuit layer 115 is folded in the second region 700 of the second circuit layer 115 without any other structure, the wire may be disconnected (open) due to the thickness of the second circuit layer 115 itself.

Accordingly, two structures, which will be described below, may be applied to prevent the wire formed in the second circuit layer 115 from being disconnected (open) and to effectively design the pitch of the transducer element in one row.

The first of the two structures is a structure in which the plurality of wires 500 extending along one row extends through other adjacent rows and is distributed. The second of the two structures is a structure in which the plurality of wires 500 respectively formed in the plurality of sub-circuit layers in the first region 600 of the second circuit layer 115 is formed in a single layer in the second region 700 of the second circuit layer 115.

Hereinafter, a structure in which a plurality of wires 500 extending along one row passes through other adjacent rows and is distributed will be described in detail.

Referring to FIGS. 8 and 11, the first region 600 of the second circuit layer 115 may be provided such that the plurality of wires 500 extending along rows of the odd element X among the transducer elements consisting of a pair of rows, that is, the base pair elements passes through rows of the even element Y and is distributed.

That is, when the plurality of wires 500 of the second circuit pattern P2 formed along the rows of the odd elements X in the first region 600 of the second circuit layer 115 extends to the second region 700 of the second circuit layer 115, the wires 500 may extend not only to the rows of the odd element X but also to the rows of the even element Y.

Hereinafter, locations and directions in which the plurality of wires 500 is distributed will be described in detail.

Referring to FIGS. 8 and 10, a region in which the plurality of wires 500 extending along one row is distributed to other adjacent rows may be defined as an edge region. The edge region may include a first edge region 610 and a second edge region 620. The first edge region 610 may be provided at one end of the first region 600 of the second circuit layer 115 adjacent to the second region 700 of the second circuit layer 115. The second edge region 620 may be provided at the other end of the first region 600 of the second circuit layer 115 adjacent to the second region 700 of the second circuit layer 115. That is, the opposite ends of the first region 600 of the second circuit layer 115 adjacent to the second regions 700 of the second circuit layer 115 in the first region 600 of the second circuit layer 115 may be defined as the first edge region 610 and the second edge region 620, respectively.

Specifically, when the plurality of wires 500 of the second circuit pattern P2 formed along the rows of the odd element X extend to the second region 700 of the second circuit layer 115, the wires 500 may pass through the rows of the even element Y from the first edge region 610 and be distributed. In this case, as illustrated in FIGS. 8 and 10, a direction of being distributed may be a first direction 610-1.

Also, when the plurality of wires 500 of the second circuit pattern P2 formed along the rows of the even element Y extend to the second region 700 of the second circuit layer 115, the wires 500 may pass through the rows of the odd element X from the second edge region 620 and be distributed. In this case, as illustrated in FIGS. 8 and 10, a direction of being distributed may be a second direction 620-1.

The first direction 610-1 and the second direction 620-1 may be parallel to a direction in which the second circuit layer 115 is folded. The first direction 610-1 and the second direction 620-1 may be opposite to each other.

That is, the first direction 610-1 may be a direction of directing to the even element Y from the odd element X. The second direction 620-1 may be a direction of directing to the odd element X from the even element Y.

As illustrated in FIGS. 8 and 10, when the wires 500 are distributed in the first direction 610-1 and the second direction 620-1, the circuit patterns formed by the plurality of wires 500 may be formed in a point symmetry based on the center of the first region 600. That is, referring to FIGS. 8 and 10, the circuit patterns may overlap when rotated 180 degrees with respect to a center 0 of the base pair element.

However, the first direction 610-1 and the second direction 620-1 are not limited to the above, but as long as the plurality of wires 500 extending along one row may pass through other adjacent rows and be distributed, the distribution direction may be various, and various pattern shapes may be formed accordingly.

In addition, when the plurality of wires 500 extend from the first region 600 to the second region 700, a distance D between the plurality of wires 500 may increase. For example, the distance D2 between the plurality of wires 500 in the second region 700 may be wider than the distance D1 of the plurality of wires in the first region 600. The plurality of wires 500 may be distributed in the first edge region 610 and/or the second edge region 620, so that a distance D between the plurality of wires 500 may be widened. Specifically, when the plurality of wires 500 are distributed in the first direction 610-1 and the second direction 620-1, the plurality of wires (500) can be distributed. The distance D2 of the plurality of electric wires distributed in the first direction 610-1 and the distance D2 of the plurality of wires 500 distributed in the second direction 620-1 are shown to be the same, but are limited thereto. It is possible to form a different distance between the plurality of wires 500.

As illustrated in FIGS. 9 and 11, the structure in which the wires 500 are distributed may be formed in the second region 700 rather than the first edge region 610 or the second edge region 620. A detailed description of the above will be described later.

Hereinafter, a structure in which the plurality of wires 500 respectively formed in the plurality of sub-circuit layers 115-1, 2 and 3 in the first region 600 of the second circuit layer 115 is formed in a single layer in the second region 700 of the second circuit layer 115 will be described.

A structure in which the first region 600 of the second circuit layer 115 includes the plurality of sub-circuit layers 115-1, 2 and 3 laminated in the axial direction A and each of the plurality of wires 500 is formed in each of the plurality of sub-circuit layers 115-1, 2, and 3 is the same as described above.

However, when without a separate structure, the plurality of sub-circuit layers 115-1, 2 and 3 laminated in the axial direction A in the first region 600 of the second circuit layer 115 is folded in the second region 700 of the second circuit layer 115, the plurality of wires 500 may be disconnected (open).

In order to solve this, the structure in which a plurality of wires 500 extending along one row passes through other adjacent rows is distributed, which is described above, and the structure in which the plurality of wires 500 respectively formed in the plurality of sub-circuit layers 115-1, 2 and 3 in the first region 600 of the second circuit layer 115 is formed in a single layer in the second region 700 of the second circuit layer 115, which will be described later, may be all applied.

A convergence layer 115-4 in which the plurality of wires 500 is gathered as one layer in the second region 700 and extends therefrom may be provided on the second circuit layer 115. The convergence layer 115-4 in the first region 600 of the second circuit layer 115 is a single layer in which the plurality of wires 500 respectively formed in the plurality of sub-circuit layers 115-1, 2, and 3 is gathered, and forming in a single layer means that the plurality of wires 500 of the second circuit pattern P2 is formed in one layer based on the axis direction A.

The convergence layer 115-4, which is a component of the second circuit layer 115, is disposed between a lower surface of the second circuit layer 114 and the sound absorbing layer 112 based on the axis direction A. Also, the convergence layer 115-4 is formed in the first edge region 610 or the second edge region 620 so that the plurality of wires 500 extends to the second region 700 of the second circuit layer 115.

The plurality of sub-circuit layers 115-1, 2 and 3 and the convergence layer 115-4 in the first region 600 of the second circuit layer 115 are layers formed in different layers based on the axis direction A, and second connection parts 116b capable of electrically connecting the above layers, respectively, may be provided.

That is, as the connection part 116 connecting each of the plurality of wires 500 of the plurality of sub-circuit layers 115-1, 2, and 3 and each of the plurality of wires 500 of the convergence layer 115-4 in the first region 600 of the second circuit layer 115, the second connection parts 116b may be provided. The shape and structure of the second connection part 116b are the same as the shape and structure of the first connection part 116a described above, and only the connection objects are different, and thus a detailed description thereof will be omitted.

The number of second connection parts 116b may respond to the number of the plurality of wires 500 disposed in the plurality of sub-circuit layers 115-1, 2, and 3 in the first region 600 of the second circuit layer 115.

For example, when the transducer module 110 forms an ultrasonic 5×4 array in the E-L plane, three wires are required in the second circuit layer 115 corresponding to the transducer element consisting of one row, and thus three of the second connection parts 116b may be provided to correspond thereto.

The second connection part 116b may be formed in the first edge region 610 or the second edge region 620 corresponding to a location where the convergence layer 115-4 is provided. The formation direction thereof may form a line along the first direction 610-1 and the second direction 620-1. The definition of the first direction 610-1 and the definition of the second direction 620-1 are the same as described above.

Because the plurality of wires 500 is dispersed in the second region 700 and formed in a single layer by the above structure, even when the second circuit layer is folded, disconnection (open) of the plurality of wires 500 may be prevented.

In addition, through the structure in which the respective wires are formed on the plurality of sub-circuit layers 115-1, 2, and 3 provided with different layers in the second circuit layer 115 and the structure in which the plurality of wires 500 extending along one row passes through other adjacent rows and is distributed, the need for securing the thickness of the wire and the gap between the wires is reduced, so that the restrictions in designing the pitch of the transducer element in one row may be reduced.

As illustrated in FIGS. 9, 11 and 13, the structure in which the plurality of wires 500 extending along one row passes through other adjacent rows and is distributed may be formed in the second region 700 rather than the first edge region 610 or the second edge region 620.

As the distribution structure is formed in the second region 700, an advantage in the dicing process may be achieved.

As described above, the piezoelectric layer 111 may be processed into a multidimensional array of a matrix form forming a plurality of rows by the dicing process. In this case, the piezoelectric layer 111 may be divided into the plurality of piezoelectric elements 111a by the kerfs 118a and 118b.

As described above, in particular, the first kerfs 118a may be divided into a case where the first kerfs 118a-1 (FIGS. 8 to 11) are formed between the base pair elements and a case where the second kerfs 118a-2 (FIGS. 8 to 11) are formed between two rows of the base pair element to be formed in different forms.

However, as in FIGS. 9 and 11, when the structure in which the plurality of wires 500 extending along one row passes through other adjacent rows and is distributed is formed in the second region 700, efficiency in the dicing process in forming the second kerf 118a-2 may be achieved.

Specifically, as illustrated in FIGS. 8 and 10, when the structure in which the plurality of wires 500 extending along one row passes through other adjacent rows and is distributed is formed in the first edge region 610 or the second edge region 620 of the first region 600, the second kerf 118a-2 formed between two rows of the base pair element may be formed to separate at least one of the matching layer 113, the enhanced layer 117, the first circuit layer 114, and the insulating layer 119, as well as the piezoelectric layer 111. That is, the second kerf 118a-2 may not be formed on the second circuit layer 115.

This is because in dicing the piezoelectric body 111 in the first region 600 provided to be selectively in contact with the plurality of piezoelectric elements 111a and 111b, some of the plurality of wires 500 may be disconnected (open) when the dicing process is applied to the second kerf 118a-2 and the second circuit layer 115 like the first kerf 118a-1.

Therefore, difficulty in process in which the first kerf 118a-1 and the second kerf 118a-2 need to have different depths at which kerf is formed despite the dicing process having the same direction may exist.

As illustrated in FIGS. 9, 11 and 13, when the structure in which the plurality of wires 500 extending along one row passes through other adjacent rows and is distributed is formed in the second region 700, the possibility of a disconnection (open) is lowered, so that like the first kerf 118a-1, the second kerf 118a-2 may also be formed in a certain region of the second circuit layer 115. Accordingly, the dicing process may be performed such that the first kerf 118a-1 and at the same time the second kerf 118a-2 may have the same direction and have the same kerf depth, thereby increasing the efficiency of the manufacturing process.

As is apparent from the above, in a structure of a multi-row probe, a plurality of circuit patterns can be formed to converage to a single layer at opposite sides of a lower portion of a piezoelectric element even when the plurality of circuit patterns is provided in a lamination structure, so that disconnection (open) of the plurality of circuit patterns can be prevented.

Further, constraints in design specifications of the circuit pattern can be reduced by utilizing an empty region of an adjacent row based on each transducer element.

Although a few embodiments of the disclosure have been shown and described, it would be appreciated by those skilled in the art that changes may be made in these embodiments without departing from the principles and spirit of the disclosure in the scope of which is defined in the claims and their equivalents.

What is claimed is:

1. An ultrasonic probe comprising:
piezoelectric elements forming a plurality of rows arranged to form a pair along a lateral direction;
a kerf formed between the piezoelectric elements along the lateral direction;
a first circuit layer disposed below the piezoelectric elements;
a second circuit layer disposed to be spaced below the first circuit layer and comprising a plurality of wires extending along the rows, the second circuit layer being provided with a first region in selectively contact with the piezoelectric elements and a second region disposed at opposite ends of the first region and folded without being in contact with the piezoelectric elements; and
a first connection part to electrically connect the first circuit layer and the second circuit layer;
wherein the first region is, when the plurality of wires extending along one row of the pair of rows extends from the first region to the second region, provided such that the plurality of wires is distributed to the other adjacent row.

2. The ultrasonic probe according to claim 1, wherein the second circuit layer is provided such that the plurality of wires is parallel in a single layer.

3. The ultrasonic probe according to claim 1, wherein the piezoelectric elements form a plurality of columns along an elevation direction, and the plurality of wires respectively corresponds to the plurality of rows.

4. The ultrasonic probe according to claim 3, wherein the first region of the second circuit layer comprises a plurality of sub-circuit layers laminated in an axial direction, and
each of the plurality of wires is formed in each of the plurality of sub-circuit layers.

5. The ultrasonic probe according to claim 4, wherein the second circuit layer further comprises a convergence layer in which the plurality of wires is gathered as one layer in the second region and extends therefrom.

6. The ultrasonic probe according to claim 5, further comprising
a second connection part to connect each of the sub-circuit layers and the convergence layer.

7. The ultrasonic probe according to claim 6, wherein the plurality of wires is distributed from the second region, and
the second connection part is formed in the folded second region.

8. The ultrasonic probe according to claim 6, wherein the first region comprises a first edge region formed at one end of the first region adjacent to the second region and a second edge region formed at the other end of the first region adjacent to the second region, and the plurality of wires is distributed from at least one of the first edge region and the second edge region.

9. The ultrasonic probe according to claim 8, wherein the second connection part is formed in at least one of the first edge region and the second edge region.

10. The ultrasonic probe according to claim 8, wherein the plurality of wires extending along one row of the pair of rows is distributed in a first direction from the first edge region, and the plurality of wires extending along the other row is distributed in a second direction from the second edge region, and
the first direction and the second direction are parallel to a direction in which the second circuit layer is folded.

11. The ultrasonic probe according to claim 10, wherein the first direction and the second direction are opposite to each other.

12. The ultrasonic probe according to claim 11, wherein circuit patterns formed by the plurality of wires are formed in a point symmetry with respect to the center of the first region.

13. The ultrasonic probe according to claim 8, wherein a distance between the plurality of wire is widened while being distributed to the first edge region or the second edge region, and
the distance between the plurality of wire in the second region is greater than the distance between the plurality of wire in the first region.

14. The ultrasonic probe according to claim 6, wherein at least one of the first connection part and the second connection part comprises a conductive hole, and
the conductive hole is filled with a conductive material, and connects a wire formed in the first circuit layer and the plurality of wires formed in the second circuit layer.

15. The ultrasonic probe according to claim 1, further comprising
an enhanced layer disposed between the piezoelectric elements and the first circuit layer.

16. The ultrasonic probe according to claim 6, wherein at least one of the first connection part or the second connection part electrically connects the first circuit layer and the second circuit layer or the second circuit layer and the convergence layer by at least one of conductive paste, conductive plating, sputtering, or printing.

17. An ultrasonic probe comprising:
piezoelectric elements forming a plurality of rows arranged to form a pair along a lateral direction and forming a plurality of columns along an elevation direction; and
a circuit layer disposed below the piezoelectric elements and comprising a plurality of wires respectively corresponding to and extending from the plurality of columns along the rows, the circuit layer being provided with a first region in selectively contact with the piezoelectric elements and a second region disposed at opposite ends of the first region and folded without being in contact with the piezoelectric elements,
wherein the first region is, when the plurality of wires extending along one row of the pair of rows extends from the first region to the second region, provided such that the plurality of wires is distributed to the other adjacent row.

18. The ultrasonic probe according to claim 17, wherein the circuit layer further comprises a convergence layer in which the plurality of wires is gathered as one layer in the second region and extends therefrom.

19. The ultrasonic probe according to claim 18, further comprising
a connection part to connect each of sub-circuit layers and the convergence layer.

* * * * *